(12) United States Patent
Iwama et al.

(10) Patent No.: US 11,499,968 B2
(45) Date of Patent: Nov. 15, 2022

(54) NANOPARTICLE MEASUREMENT DEVICE, ANALYSIS DEVICE, AND ANALYSIS METHOD

(71) Applicant: JVC KENWOOD Corporation, Yokohama (JP)

(72) Inventors: Shigehiko Iwama, Yokohama (JP); Masahiro Yamamoto, Yokohama (JP); Atsushi Saito, Yokohama (JP)

(73) Assignee: JVC KENWOOD CORPORATION, Yokohama (JP)

( * ) Notice: Subject to any disclaimer, the term of this patent is extended or adjusted under 35 U.S.C. 154(b) by 935 days.

(21) Appl. No.: 16/284,169

(22) Filed: Feb. 25, 2019

(65) Prior Publication Data

US 2019/0293640 A1    Sep. 26, 2019

(30) Foreign Application Priority Data

Mar. 26, 2018 (JP) .............................. JP2018-058391

(51) Int. Cl.
*G01N 33/543* (2006.01)
*G01N 35/00* (2006.01)

(52) U.S. Cl.
CPC . *G01N 33/54373* (2013.01); *G01N 33/54353* (2013.01); *G01N 33/54366* (2013.01); *G01N 33/54386* (2013.01); *G01N 35/00069* (2013.01)

(58) Field of Classification Search
None
See application file for complete search history.

(56) References Cited

U.S. PATENT DOCUMENTS

| 7,812,318 | B1 | 10/2010 | Auld |
| 2005/0037484 | A1 | 2/2005 | Staimer et al. |
| 2005/0111328 | A1 | 5/2005 | Potyrailo et al. |
| 2008/0304073 | A1 | 12/2008 | Nolte et al. |
| 2018/0321227 | A1* | 11/2018 | Iwama ............. G01N 33/54366 |

FOREIGN PATENT DOCUMENTS

| JP | 2001126261 A | 5/2001 |
| JP | 2015127691 A | 7/2015 |
| WO | 2017056526 A1 | 4/2017 |
| WO | 2017134944 A1 | 8/2017 |

OTHER PUBLICATIONS

Extended European Search Report dated Aug. 13, 2019 corresponding to application No. 19164799.9-1020.

* cited by examiner

*Primary Examiner* — Ann Montgomery
(74) *Attorney, Agent, or Firm* — Nath, Goldberg & Meyer; Jerald L. Meyer

(57) ABSTRACT

A nanoparticle measurement device includes a timing signal generation unit, a low-frequency component extraction unit, a low-frequency component calculation unit, a threshold correction unit, and a measurement unit. The timing signal generation unit generates timing signals. The low-frequency component extraction unit extracts low-frequency components according to the timing signals. The low-frequency component calculation unit calculates an interpolated low-frequency component in accordance with the low-frequency components. The threshold correction unit sets a corrected threshold in accordance with the interpolated low-frequency component. The measurement unit extracts and counts nanoparticle pulse signals from a light reception signal according to the timing signals and the corrected threshold.

6 Claims, 18 Drawing Sheets

NANOPARTICLE MEASUREMENT DEVICE, ANALYSIS DEVICE, AND ANALYSIS METHOD

CROSS REFERENCE TO RELATED APPLICATION

This application is based upon and claims the benefit of priority under 35 U.S.C. § 119 from Japanese Patent Application No. 2018-058391 filed on Mar. 26, 2018, the entire contents of all of which are incorporated herein by reference.

BACKGROUND

The present disclosure relates to a nanoparticle measurement device, an analysis device, and an analysis method for analyzing biomaterials such as antigens and antibodies.

Immunoassays are known to quantitatively analyze disease detection and therapeutic effects by detecting particular antigens or antibodies as biomarkers associated with diseases.

Japanese Unexamined Patent Application Publication No. 2015-127691 discloses an analysis device in which antibodies that are fixed to a reaction region on a disc for specimen analysis are allowed to bind to antigens in a sample, and the antigens are labeled by nanoparticles having antibodies and then are scanned with laser light emitted from an optical pickup so as to detect the nanoparticles captured on the reaction region. The analysis device disclosed in Japanese Patent Application Publication No. 2015-127691 is an optical disc device utilized for detecting a specimen.

SUMMARY

The specimen analysis disc may be warped during the process of forming the reaction region on the disc. The warp of the specimen analysis disc causes a tilt on the surface on which the reaction region is formed. When the warped specimen analysis disc is scanned with the laser light, detection signals for detecting nanoparticles captured on the reaction region cause fluctuation of low-frequency components because of the tilt on the surface of the specimen analysis disc. The fluctuation of the low-frequency components decreases the accuracy of detecting the nanoparticles. The warp of the specimen analysis disc thus leads to the deterioration of detection accuracy of nanoparticles.

Japanese Unexamined Patent Application Publication No. 2001-126261 discloses an optical disc device with a reduced influence of a warp on an optical disc. The optical disc device disclosed in Japanese Patent Application Publication No. 2001-126261 can reduce the influence of the warp on the optical disc in the radial direction, but cannot deal with the influence of the warp in the tangential direction.

A first aspect of one or more embodiments provides a nanoparticle measurement device including: a timing signal generation unit configured to generate a first timing signal corresponding to a first track interval in a reaction region formed in a disc for specimen analysis having a plurality of tracks on which nanoparticles binding to substances to be detected are captured per track, and a second timing signal corresponding to a second track interval different from the reaction region, the tracks being formed from an inner side to an outer side of the disc for specimen analysis; a low-frequency component extraction unit configured to extract a low-frequency component fluctuating because of a warp of the disc for specimen analysis from a light reception signal according to the second timing signal, the light reception signal being generated when a laser light is radiated to the reaction region and a reflected light is received from the reaction region; a low-frequency component calculation unit configured to calculate an interpolated low-frequency component corresponding to the first track interval and interpolated in accordance with the low-frequency component; a threshold correction unit configured to correct a predetermined threshold in accordance with the interpolated low-frequency component to set a corrected threshold; and a measurement unit configured to extract nanoparticle pulse signals from the light reception signal according to the first timing signal and the corrected threshold, and count the nanoparticle pulse signals, so as to count the nanoparticles captured in the first track interval in the reaction region.

A second aspect of one or more embodiments provides an analysis device including: a turntable holding a disc for specimen analysis; a turntable drive unit configured to rotate the turntable; a turntable drive circuit configured to control the turntable drive unit; an optical pickup driven in a direction perpendicular to a rotation axis of the turntable, and configured to emit a laser light to a reaction region, receive a reflected light from the reaction region, and generate a light reception signal; an optical pickup drive circuit configured to control an operation of the optical pickup; and a controller configured to control the turntable drive circuit and the optical pickup drive circuit, wherein the controller comprises the above-described nanoparticle measurement device.

A third aspect of one or more embodiments provides an analysis method including: rotating a disc for specimen analysis having a plurality of tracks formed from an inner side to an outer side and having a reaction region on which nanoparticles binding to substances to be detected are captured per track; radiating a laser light to the reaction region per track; receiving a reflected light from the reaction region to generate a light reception signal; generating a first timing signal corresponding to a first track interval in the reaction region, and a second timing signal corresponding to a second track interval different from the reaction region; extracting a low-frequency component fluctuating because of a warp of the disc for specimen analysis from the light reception signal according to the second timing signal; calculating an interpolated low-frequency component corresponding to the first track interval and interpolated in accordance with the low-frequency component; correcting a predetermined threshold in accordance with the interpolated low-frequency component to set a corrected threshold; extracting nanoparticle pulse signals from the light reception signal according to the first timing signal and the corrected threshold; and counting the nanoparticle pulse signals so as to count the nanoparticles captured in the first track interval in the reaction region.

DETAILED DESCRIPTION

[Detection-Target-Substance Capture Unit]

Figure 1:
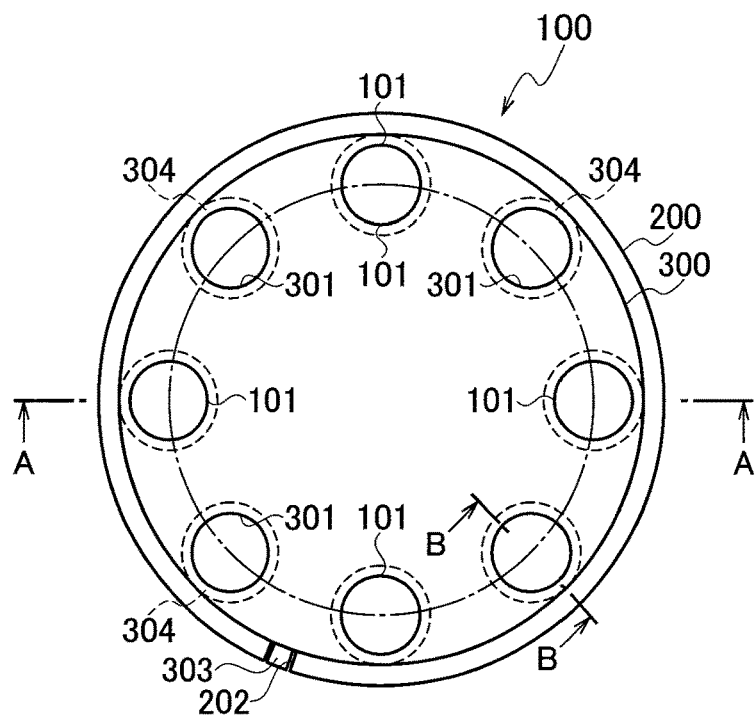
FIG. 1 is a plan view illustrating a structure of a detection-target-substance capture unit.
Figure 2:
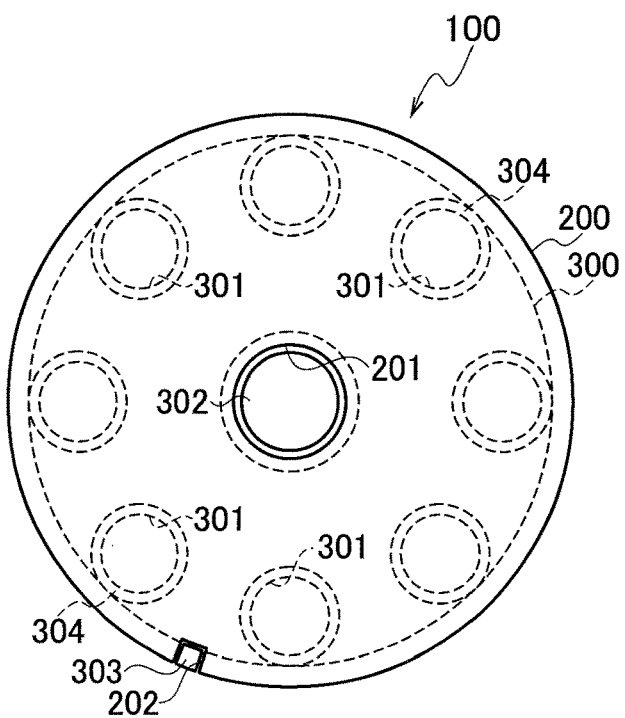
FIG. 2 is a plan view illustrating the structure of the detection-target-substance capture unit.
Figure 3A:
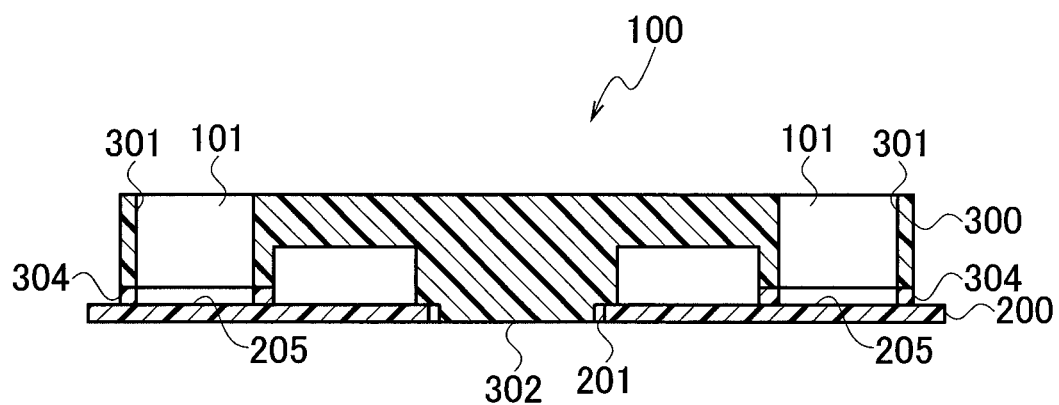
FIG. 3A is a cross-sectional view of the detection-target-substance capture unit taken along line A-A in FIG. 1.
Figure 3B:
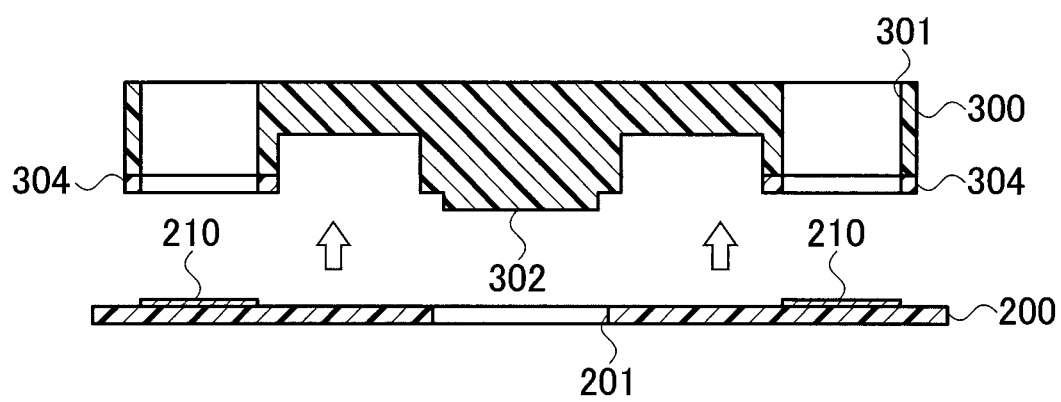
FIG. 3B is a cross-sectional view showing a state in which a cartridge is removed from a disc for specimen analysis.
Figure 4:
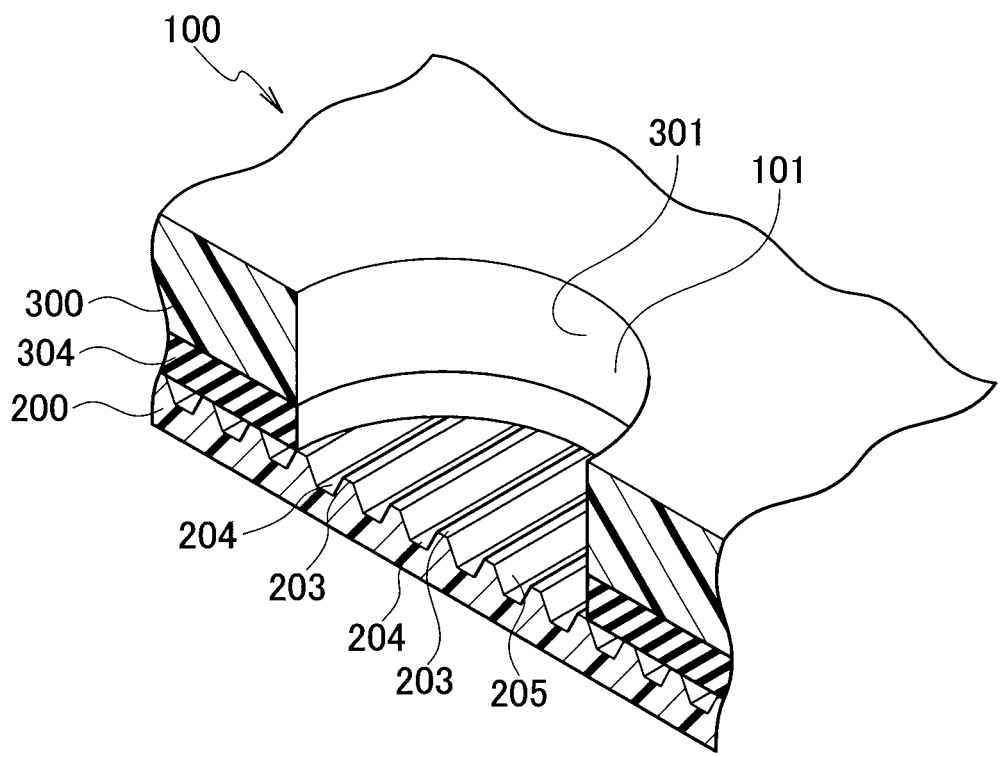
FIG. 4 is an enlarged perspective view showing a well cross-sectioned along line B-B in FIG. 1.

A detection-target-substance capture unit is illustrated below with reference to FIG. 1, FIG. 2, FIG. 3A, FIG. 3B, and FIG. 4. FIG. 1 is a view showing the detection-target-substance capture unit as viewed from the cartridge side. FIG. 2 is a view showing the detection-target-substance capture unit as viewed from the specimen analysis disc side. FIG. 3A is a cross-sectional view of the detection-target-substance capture unit taken along line A-A in FIG. 1. FIG. 3B is a view illustrating a state in which the cartridge is removed from the specimen analysis disc. FIG. 4 is a partly-enlarged view of a well shown in FIG. 1 taken along line B-B in FIG. 1.

As shown in FIG. 1 and FIG. 2, the detection-target-substance capture unit 100 includes the specimen analysis disc 200 and the cartridge 300. The specimen analysis disc 200 is formed into a circular shape having substantially the same dimensions as optical discs such as Blu-ray discs (BDs), DVDs, and compact discs (CDs). The specimen analysis disc 200 is formed of resin material such as polycarbonate resin and cycloolefin polymer, commonly used for optical discs. The specimen analysis disc 200 is not limited to the optical discs described above, and may be any optical disc according to other embodiments or conforming to prescribed standards.

As shown in FIG. 1, FIG. 2, FIG. 3A, or FIG. 3B, the specimen analysis disc 200 has a center hole 201 formed in the middle of the disc, and a slit 202 provided at the circumferential edge of the disc. The slit 202 serves as a reference-position defining portion for defining a reference position of the specimen analysis disc 200.

As shown in FIG. 4, the surface of the specimen analysis disc 200 includes track regions 205 provided with convex regions 203 and recesses 204 alternately arranged in a radial direction. The convex regions 203 and the recesses 204 are formed in a spiral or concentric state from the inner side to the outer side of the specimen analysis disc 200. The convex regions 203 correspond to lands of an optical disc. The recesses 204 correspond to grooves of an optical disc, and correspond to tracks of the specimen analysis disc 200. The specimen analysis disc 200 thus includes a plurality of tracks formed from the inner side to the outer side. A track pitch of the recesses 204 in the radial direction is 320 nanometers (nm), for example.

As shown in FIG. 1, FIG. 2, FIG. 3A, or FIG. 3, the cartridge 300 is provided with a plurality of cylindrical penetration holes 301 along the circumferential direction. The penetration holes 301 are arranged at regular intervals such that the respective center points are located on the common circle. The cartridge 300 includes a convex portion 302 in the middle, a convex portion 303 at the circumferential edge, and a plurality of seal members 304 corresponding to the penetration holes 301 at the circumferential edge. The seal members 304 are ring-like gaskets formed of elastically-deformable material such as silicone rubber, for example. As shown in FIG. 3A, FIG. 3B, or FIG. 4, the seal members 304 are placed around the respective penetration holes 301.

When the cartridge 300 is attached to the specimen analysis disc 200, the convex portion 302 is inserted into the center hole 201 of the specimen analysis disc 200, and the convex portion 303 is inserted into the slit 202 so as to position the cartridge 300 and the specimen analysis disc 200 together. When the cartridge 300 is attached to the specimen analysis disc 200, the seal members 304 are elastically deformed to fill the recesses 204 of the track regions 205. FIG. 4 illustrates a state before the seal member 304 is elastically deformed.

As shown in FIG. 3A and FIG. 4, the detection-target-substance capture unit 100 includes a plurality of wells 101 defined by the insertion holes 301 of the cartridge 300 together with the track regions 205 of the specimen analysis disc 200. The side surfaces on the inner side (inner surfaces) of the insertion holes 301 correspond to the inner surfaces of the wells 101, and the track regions 205 of the specimen analysis disc 200 correspond to the bottoms of the wells 101.

The wells 101 each serve as a holder for storing a solution such as a sample solution, a buffer solution, and a cleaning solution. The seal members 304 decrease a risk of leakage of the solution from the wells 101. Although FIG. 1 and FIG.

2 illustrate the detection-target-substance capture unit 100 including eight wells 101, the number of wells 101 is not limited to eight.

As shown in FIG. 3B, the cartridge 300 is detachable from the specimen analysis disc 200. Nanoparticles for labeling substances to be detected are detected and measured only by use of the specimen analysis disc 200 separated from the cartridge 300.

[Formation of Reaction Regions]

An example of a method of forming reaction regions is described below with reference to the flow charts of FIG. 5 and FIG. 6. The operator injects a buffer solution including antibodies 111 into the wells 101 of the detection-target-substance capture unit 100. The operator incubates the solution in the detection-target-substance capture unit 100 for an appropriate time at an appropriate temperature.

The antibodies 111 are thus fixed to the track regions 205 of the specimen analysis disc 200 which are the bottoms of the wells 101. The operator drains the buffer solution from the wells 101, and cleans the wells 101 with another buffer solution or a cleaning solution. The antibodies 111 not fixed to the track regions 205 are removed by the cleaning.

The operator injects a sample solution including detection target substances 121 into the wells 101. The detection target substances 121 are exosomes, for example. The sample solution sometimes does not include the detection target substances 121. The following is the case in which the sample solution includes the detection target substances 121 for illustration purposes.

The operator incubates the solution in the detection-target-substance capture unit 100 for an appropriate time at an appropriate temperature. The detection target substances 121 are then specifically bound to the antibodies 111 fixed to the track regions 205 by an antigen-antibody reaction. The detection target substances 121 are thus captured on the track regions 205.

The operator drains the sample solution from the wells 101, and cleans the wells 101 with a buffer solution or a cleaning solution. The detection target substances 121 not bound to the antibodies 111 but dispersed in the sample solution, and the detection target substances 121 adhering to the track regions 205 by non-specific binding, which is not the antigen-antibody reaction, are removed by the cleaning.

The operator injects a buffer solution including nanoparticles 131 serving as labels into the wells 101. The surfaces of the nanoparticles 131 are provided with antibodies which specifically bind to the detection target substances 121 by the antigen-antibody reaction. The operator incubates the solution in the detection-target-substance capture unit 100 for an appropriate time at an appropriate temperature.

The nanoparticles 131 specifically bind to the detection target substances 121 captured on the track regions 205 by the antigen-antibody reaction. The nanoparticles 131 binding to the detection target substances 121 are thus captured on the track regions 205, more particularly, on the recesses 204 of the track regions 205.

The operator drains the buffer solution from the wells 101, cleans the wells 101 with another buffer solution or a cleaning solution, and dries the wells 101. The nanoparticles 131 not binding to the detection target substances 121 but dispersed in the buffer solution are removed by the cleaning.

The operator separates the cartridge 300 and the specimen analysis disc 200 of the detection-target-substance capture unit 100, as shown in FIG. 3B. The specimen analysis disc 200 is provided with a plurality of circular reaction regions 210 corresponding to the respective wells 101.

Figure 5:
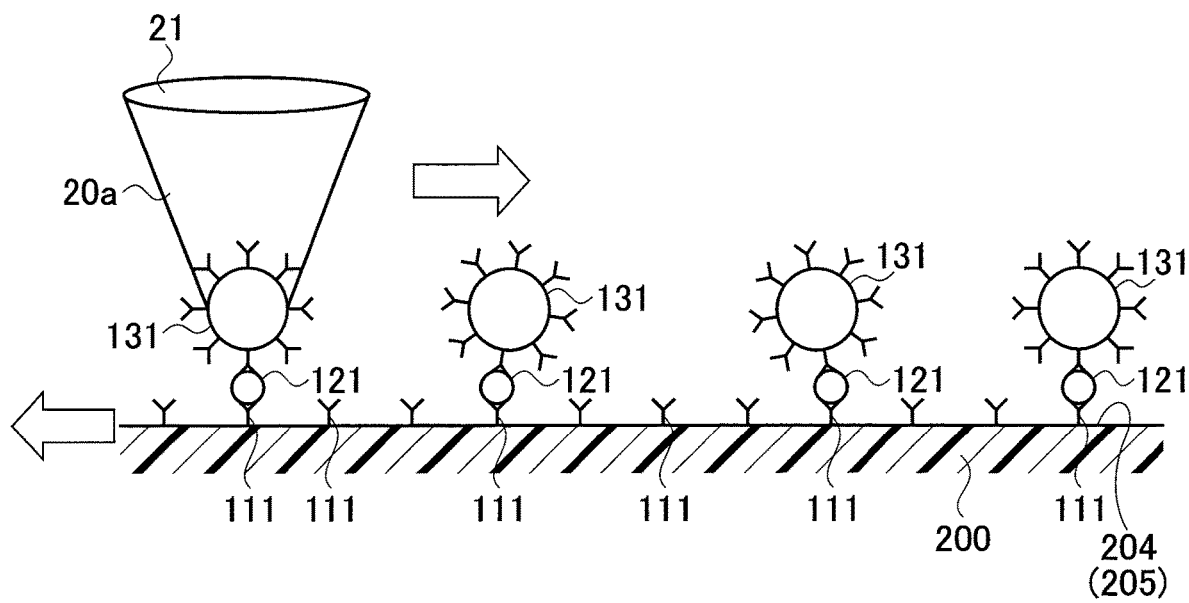
FIG. 5 is a schematic cross-sectional view showing a state in which substances to be detected are captured and sandwiched between antibodies and nanoparticles in a recess of a track region.
Figure 6:
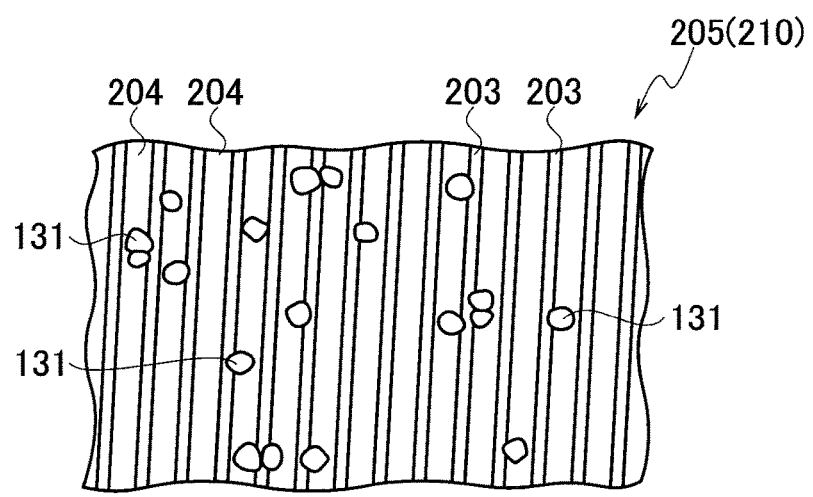
FIG. 6 is a schematic plan view showing a state in which the nanoparticles and the substances to be detected coupled together are captured in recesses of the track region.

As shown in FIG. 5, the nanoparticles 131 binding to the detection target substances 121 are captured on the recesses 204 of the track regions 205 in the reaction regions 201. The detection target substances 121 are captured and sandwiched between the antibodies 111 and the nanoparticles 131 on the recesses 204 of the track regions 205. FIG. 6 illustrates a state in which the nanoparticles 131 binding to the detection target substances 121 are captured on the recesses 204 of the track region 205.

First Embodiment

A nanoparticle measurement device, an analysis device, and an analysis method according to a first embodiment are described below with reference to FIG. 7, FIG. 8A, FIG. 8B, FIG. 8C, FIG. 9, FIG. 10, FIG. 11, FIG. 12, and FIG. 13. First, the analysis device according to a first embodiment is described with reference to FIG. 7. When the detection target substances 121 are exosomes having a size as small as 100 nm, it is difficult to optically detect the detection target substance 121 directly. The analysis device according to a first embodiment detects and measures the nanoparticles 131 captured on the reaction regions 210 so as to indirectly detect and measure the detection target substances 121 specifically bound to the nanoparticles 131.

Figure 7:
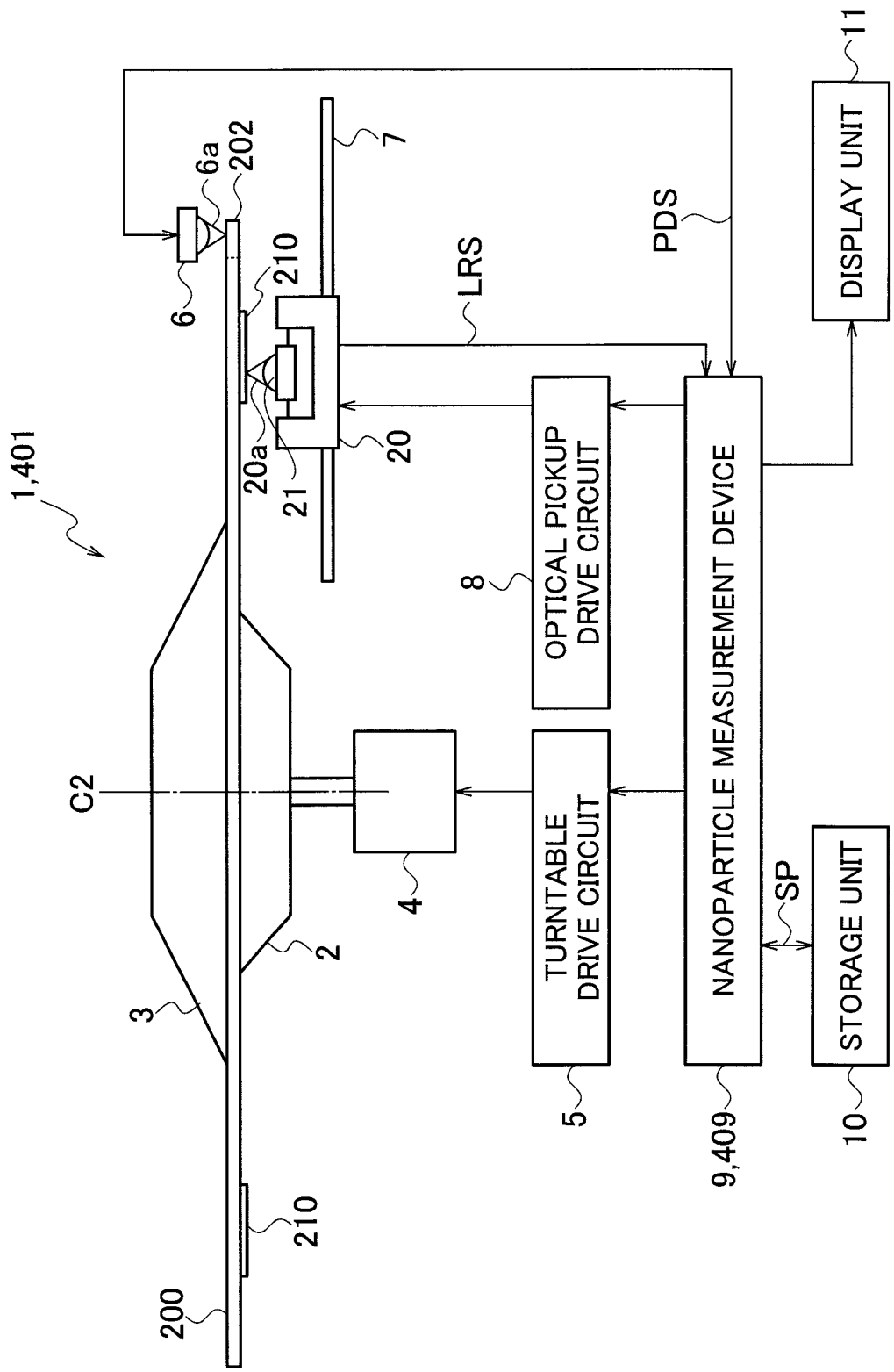
FIG. 7 is a configuration diagram illustrating an analysis device according to first and second embodiments.

As shown in FIG. 7, the analysis device 1 includes a turntable 2, a clamper 3, a turntable drive unit 4, a turntable drive circuit 5, and a reference-position detection sensor 6. The analysis device 1 further includes a guide shaft 7, an optical pickup 20, an optical pickup drive circuit 8, a nanoparticle measurement device 9, a storage unit 10, and a display unit 11. The analysis device 1 does not necessarily include the display unit 11, and an external display unit may be used instead.

The specimen analysis disc 200 is placed on the turntable 2 with the reaction regions 210 facing down. The clamper 3 is driven in directions separating from and approaching the turntable 2. The specimen analysis disc 200 is held by the clamper 3 and the turntable 2 when the clamper 3 is driven in the direction approaching the turntable 2.

The turntable drive unit 4 drives the turntable 2 to rotate on the rotation axis C2 together with the specimen analysis disc 200 and the clamper 3. A spindle motor may be used as the turntable drive unit 4. The turntable drive circuit 5 controls the turntable drive unit 4. For example, the turntable drive circuit 5 controls the turntable drive unit 4 such that the turntable 2 rotates at a constant linear velocity together with the specimen analysis disc 200 and the clamper 3.

The reference-position detection sensor 6 is placed adjacent to the circumferential portion of the specimen analysis disc 200. The reference-position detection sensor 6 is an optical sensor such as a photoreflector, for example. The reference-position detection sensor 6 emits detection light 6a toward the circumferential portion of the rotating specimen analysis disc 200, and receives the reflected light from the specimen analysis disc 200.

The reference-position detection sensor 6 detects the slit 202 of the specimen analysis disc 200, generates a reference-position detection signal PDS, and outputs the signal to the nanoparticle measurement device 9. The reference-position detection signal PDS is a pulse signal which rises to be on when the slit 202 reaches the detecting position of the reference-position detection sensor 6, namely, the position to which the detection light 6a is radiated, and falls to be off when the slit 202 passes through the detecting position.

The reference-position detection sensor 6 detects the reference position per rotation period and per track of the specimen analysis disc 200. A transmission-type optical sensor may be used as the reference-position detection sensor 6. The reference-position detection sensor 6 of this type emits the detection light 6a to the specimen analysis disc 200 and receives the detection light 6a passing through the slit 202, so as to detect the reference position per rotation period and per track of the specimen analysis disc 200.

The guide shaft 7 is placed in parallel to the specimen analysis disc 200 in the radial direction of the specimen analysis disc 200. The optical pickup 20 is supported by the guide shaft 7. The optical pickup 20 is driven along the guide shaft 7 in the direction perpendicular to the rotation axis C2 of the turntable 2, in the radial direction of the specimen analysis disc 200, and in parallel to the specimen analysis disc 200.

The optical pickup 20 includes an objective lens 21. The optical pickup 20 emits laser light 20a to the specimen analysis disc 200. The laser light 20a is condensed by the objective lens 21 on the track regions 205 provided with the reaction regions 210 on the specimen analysis disc 200. The reference numerals 21 and 20a indicated in FIG. 5 correspond to the objective lens 21 and the laser light 20a shown in FIG. 7 with the vertical direction reversed.

The optical pickup 20 is driven in the radial direction of the rotating specimen analysis disc 200. The recesses 204 corresponding to the tracks are thus scanned with the laser light 20a, as shown in FIG. 5. The optical pickup 20 receives the reflected light from the specimen analysis disc 200. The optical pickup 20 detects a light reception level of the reflected light, generates a light reception signal LRS, and outputs the signal to the nanoparticle measurement device 9.

The optical pickup drive circuit 8 controls the operation of the optical pickup 20. The optical pickup drive circuit 8 moves the optical pickup 20 along the guide shaft 7 or moves the objective lens 21 of the optical pickup 20 in the vertical direction.

The nanoparticle measurement device 9 controls the turntable drive circuit 5 and the optical pickup drive circuit 8. The nanoparticle measurement device 9 thus serves as a controller. The nanoparticle measurement device 9 controls the turntable drive circuit 5 to stop or rotate the turntable 2 at a constant linear velocity, for example.

The nanoparticle measurement device 9 controls the optical pickup drive circuit 8 to move the optical pickup 20 to a target position in the radial direction of the specimen analysis disc 200 or adjust the position of the objective lens 21 in the vertical direction so as to condense the laser light 20a on the track regions 205.

The nanoparticle measurement device 9 detects the reference position per rotation period and per track of the specimen analysis disc 200 according to the reference-position detection signal PDS output from the reference-position detection sensor 6. The nanoparticle measurement device 9 specifies the reaction regions 210 according to the reference position detected.

The storage unit 10 stores measurement parameters SP for every track in each reaction region 210. The measurement parameters SP include measurement information such as the number of the reaction regions 210, the time corresponding to the distance from the slit 202 as a reference-position defining portion to each reaction region 210, and the timing of timing signals of each track.

The nanoparticle measurement device 9 reads out the measurement parameter SP from the storage unit 10, and sequentially generates a plurality of nanoparticle measurement timing signals BTS and a plurality of low-frequency component measurement timing signals LTS, as a plurality of measurement timing signals, per track in each reaction region 210 based on the measurement parameter SP.

The nanoparticle measurement timing signals BTS are timing signals for measuring the nanoparticles 131 captured in the reaction regions 210. The low-frequency component measurement timing signals LTS are timing signals for measuring low-frequency components fluctuating because of a warp of the specimen analysis disc 200. Hereinafter, the nanoparticle measurement timing signal BTS is defined as a first timing signal, and the low-frequency component measurement timing signal LTS is defined as a second timing signal.

The nanoparticle measurement device 9 extracts nanoparticle pulse signals BS per nanoparticle measurement timing signal BTS from the light reception signal LRS output from the optical pickup 20. The method of generating the light reception signals LRS and extracting the nanoparticle pulse signals BS will be described below.

The nanoparticle measurement device 9 counts the extracted nanoparticle pulse signals BS so as to count the number of the nanoparticles 131 labeling the detection target substances 121. The nanoparticle measurement device 9 directs the storage unit 10 to store the number of the nanoparticles 131 per nanoparticle measurement timing signal BTS in each reaction region 210. The nanoparticle measurement device 9 adds up the number of the nanoparticles 131 in each reaction region 210 and displays the sum on the display unit 11. The number of the nanoparticles 131 displayed corresponds to the number of the detection target substances 121 specifically bound to the nanoparticles 131.

Figure 8A:
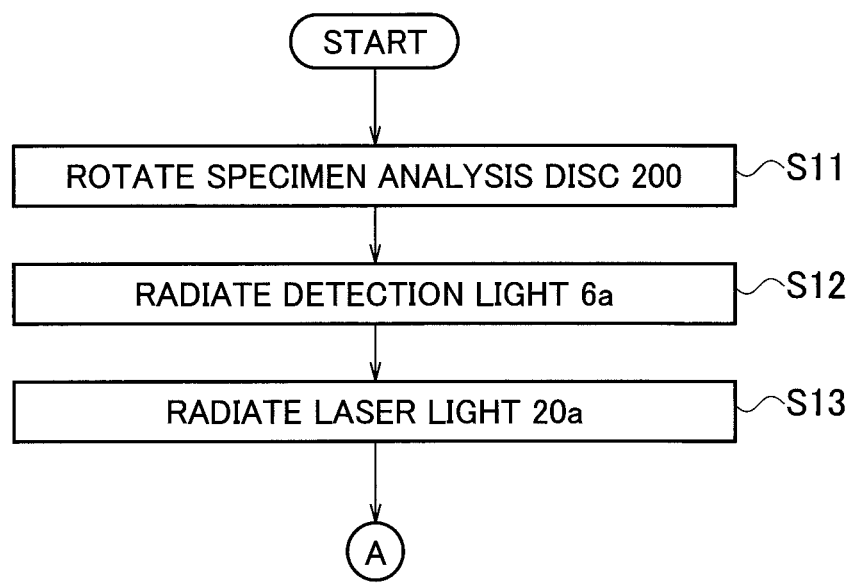
FIG. 8A is a flow chart for illustrating an analysis method by the analysis device according to a first embodiment.
Figure 8B:
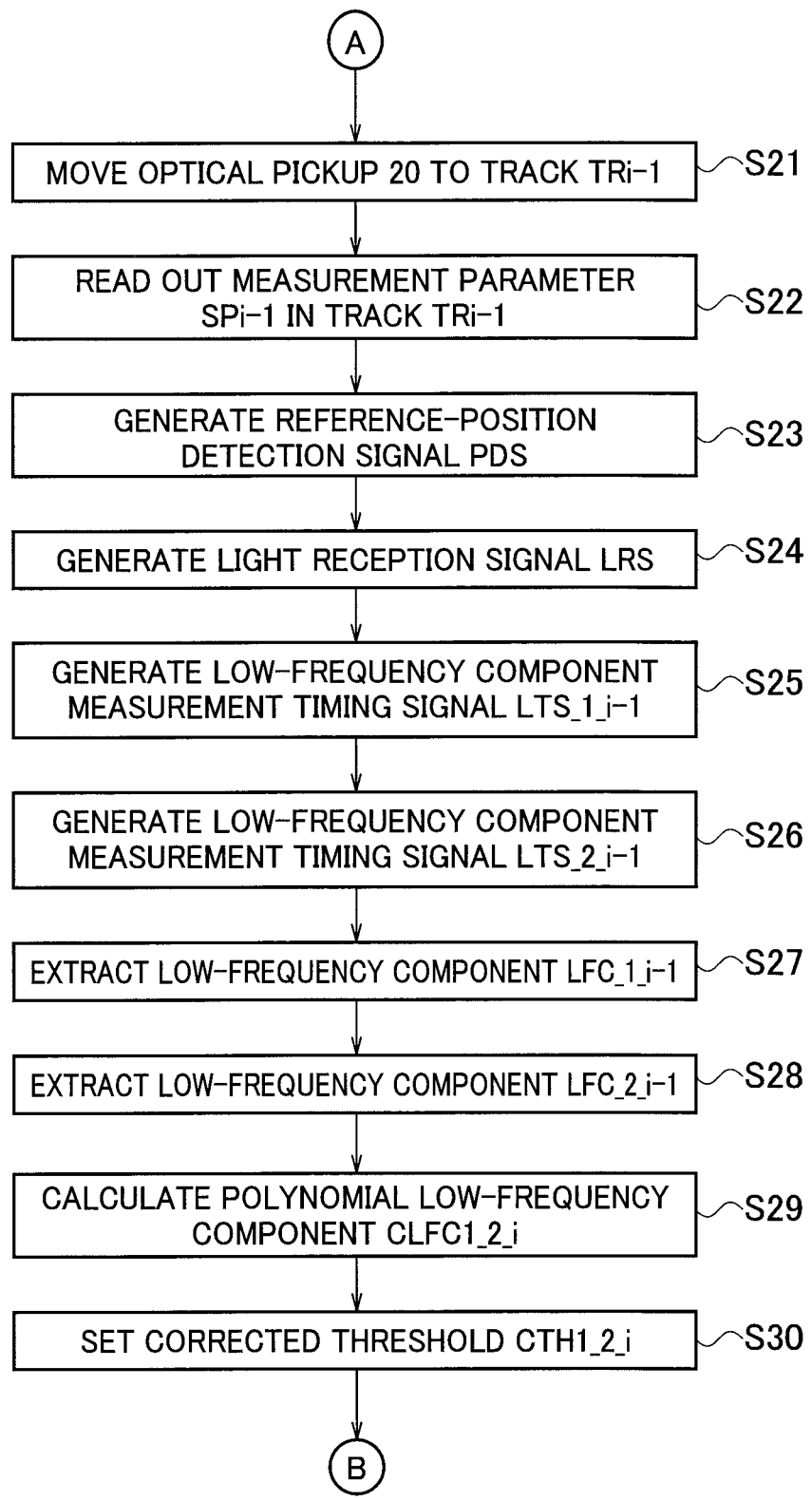
FIG. 8B is a flow chart for illustrating the analysis method by the analysis device according to a first embodiment.
Figure 8C:
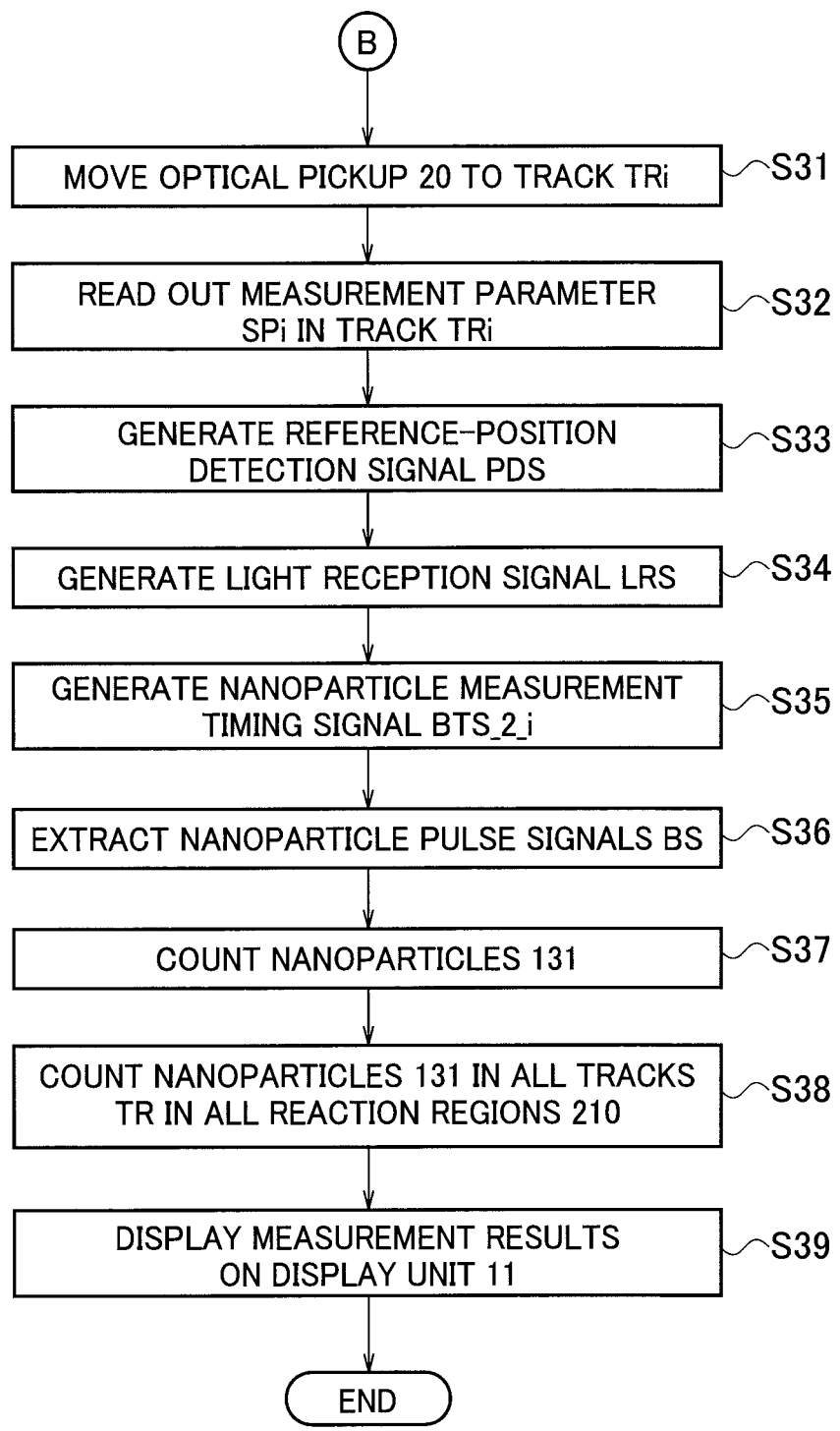
FIG. 8C is a flow chart for illustrating the analysis method by the analysis device according to a first embodiment.

The analysis method of analyzing the detection target substances 121 by the analysis device 1, more particularly the method of analyzing the nanoparticles 131 labeling the detection target substances 121, is described below with reference to FIG. 8A, FIG. 8B, FIG. 8C, FIG. 9, FIG. 10, FIG. 11, FIG. 12, and FIG. 13. FIG. 8A, FIG. 8B, and FIG. 8C are flow charts illustrating the analysis method of analyzing the detection target substances 121 by the analysis device 1.

In step S11 in the flow chart shown in FIG. 8A, the nanoparticle measurement device 9 controls the turntable drive circuit 5 to direct the turntable drive unit 4 to turn the turntable 2 so that the specimen analysis disc 200 rotates at a constant linear velocity.

In step S12, the nanoparticle measurement device 9 directs the reference-position detection sensor 6 to emit the detection light 6a to the specimen analysis disc 200. In step S13, the nanoparticle measurement device 9 directs the optical pickup 20 to emit the laser light 20a to the specimen analysis disc 200. Step S13 is not necessarily performed after step S12. Step S12 may be performed after step S13, or step S12 and step S13 may be performed simultaneously.

Figure 9:
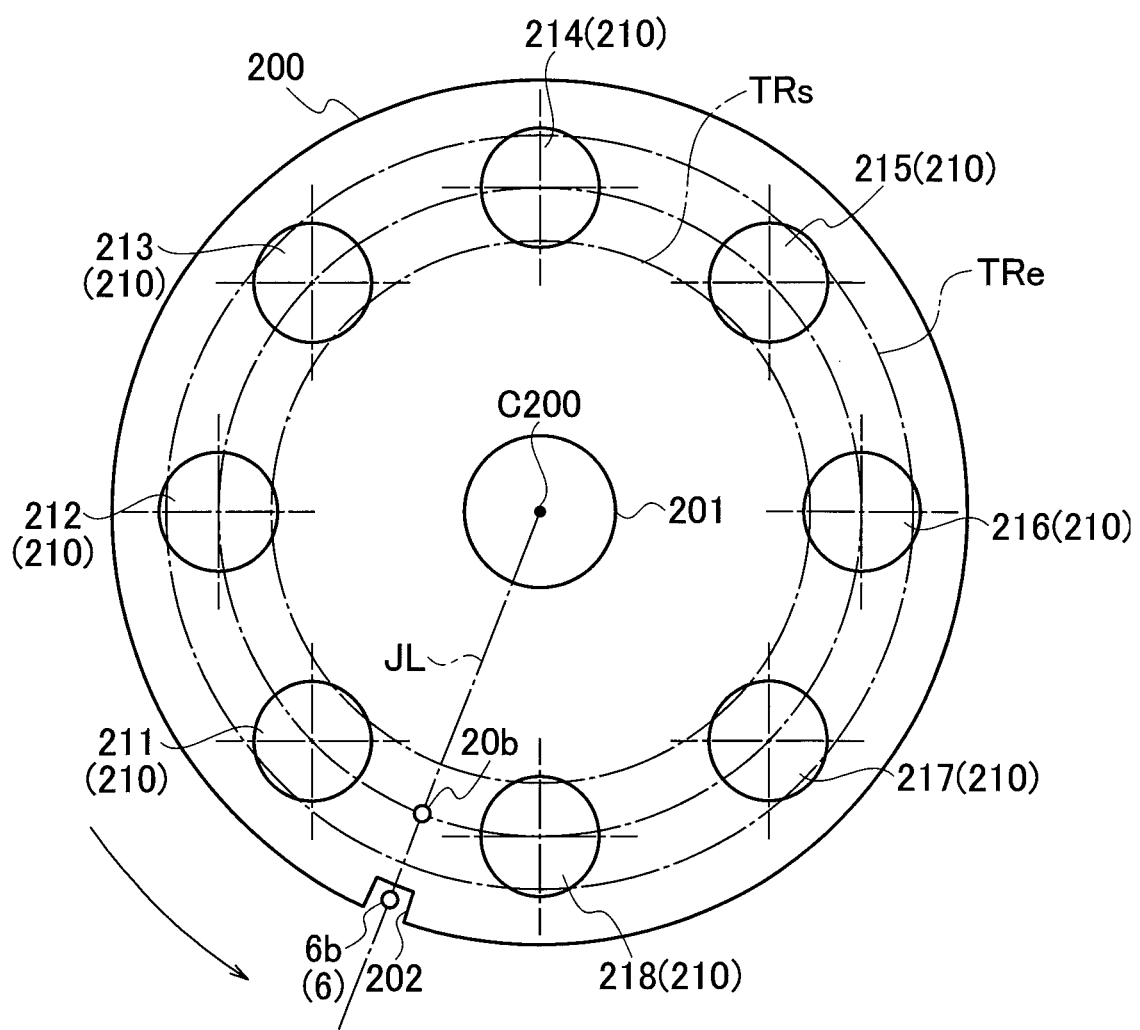
FIG. 9 is a plan view illustrating a positional relationship between detecting positions of a reference-position detection sensor and an optical pickup, and positions of a slit and reaction regions on the specimen analysis disc.

FIG. 9 schematically illustrates a positional relationship between the detecting positions of the reference-position detection sensor 6 and the optical pickup 20, and the positions of the slit 202 and the respective reaction regions 210 in the specimen analysis disc 200. The arrow in FIG. 9 indicates the rotating direction of the specimen analysis disc 200. Reference sign 6b indicates the detecting position of the reference-position detection sensor 6. The axial line JL corresponds to the guide shaft 7.

The detecting position 6b of the reference-position detection sensor 6 is located on the axial line JL in FIG. 9, but is not limited to this illustration. The detecting position 6b may be any position at which the slit 202 can be detected at the circumferential edge of the specimen analysis disc 200. The optical pickup 20 moves along the axial line JL in the radial direction of the specimen analysis disc 200. Reference sign 20b in FIG. 9 indicates the detecting position of the optical pickup 20.

As shown in FIG. 9, the reaction regions 210 are arranged at regular intervals such that the respective center points are located on the common circle having the center C200 of the specimen analysis disc 200. For distinguishing the respective reaction regions 210, the reaction region, to which the laser light 20a is radiated first after the reference-position detection sensor 6 detects the slit 202 with the detection light 6a, is indicated by reference numeral 211, and the following reaction regions, to which the laser light 20a is sequentially radiated, are indicated by reference numerals 212, 213, 214, 215, 216, 217, and 218.

The laser light 20a is radiated sequentially to the respective reaction regions 211 to 218 per track TR from the track TRs located on the inner side of the specimen analysis disc 200 to the track TRe located on the outer side of the specimen analysis disc 200.

Figure 10:
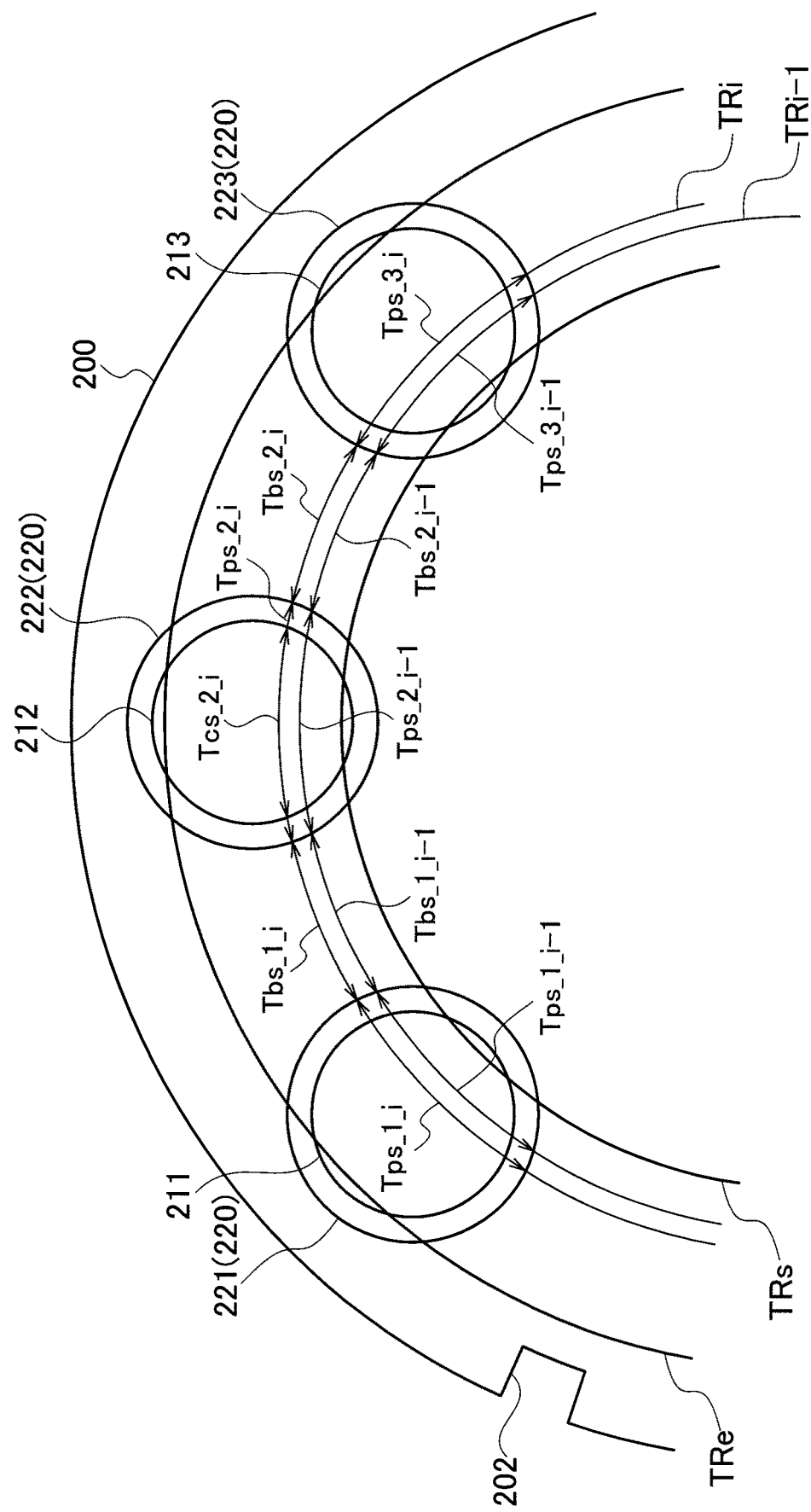
FIG. 10 is a diagram illustrating a relationship between the reaction regions, impurity regions, tracks, and track intervals.

A case of measuring the nanoparticles 131 in the track TRi (s<i<e) in the reaction region 212 is described below. FIG. 10 illustrates the reaction region 211 to which the laser light 20a is radiated first after the reference-position detection sensor 6 detects the slit 202, the reaction region 212 to which the laser light 20a is radiated after the reaction region 211, and the reaction region 213 to which the laser light 20a is radiated after the reaction region 212, for illustration purposes.

FIG. 10 illustrates a state in which the reaction regions 211, 212, and 213 are sequentially scanned with the laser light 20a along the track TRi−1 (s<i−1<e) and further along the track TRi (s<i−1<i<e). The nanoparticle measurement device 9, the analysis device 1, and the analysis method according to a first embodiment are illustrated with a case in which the track TRi is a first track, and the track TRi−1 is a second track. For illustration purposes, only signal processing of measuring the nanoparticles 131 in the track TRi (s<i<e) in the reaction region 212 is described below.

In step S21 in the flow chart shown in FIG. 8B, the nanoparticle measurement device 9 controls the optical pickup drive circuit 8 to move the optical pickup 20 above the track TRi−1 so that the laser light 20a is radiated to the track TRi−1 of the specimen analysis disc 200. The track TRi−1 is thus scanned with the laser light 20a.

Figure 11:
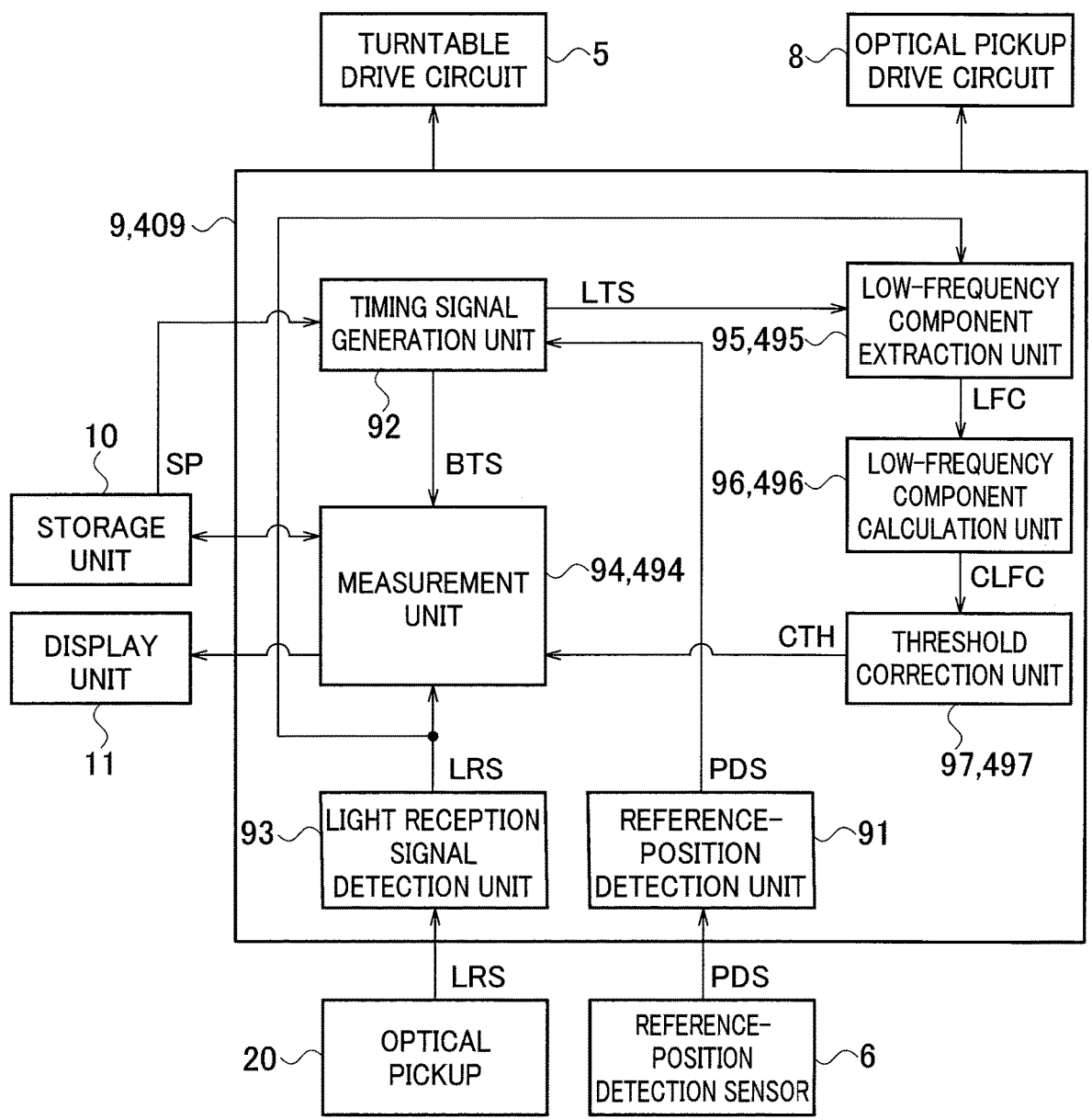
FIG. 11 is a configuration diagram illustrating a nanoparticle measurement device in the analysis device according to first and second embodiments.

FIG. 11 illustrates a configuration of the nanoparticle measurement device 9. As shown in FIG. 11, the nanoparticle measurement device 9 includes a reference-position detection unit 91, a timing signal generation unit 92, a light reception signal detection unit 93, a measurement unit 94, a low-frequency component extraction unit 95, a low-frequency component calculation unit 96, and a threshold correction unit 97.

The nanoparticle measurement device 9, and the reference-position detection unit 91, the timing signal generation unit 92, the light reception signal detection unit 93, the measurement unit 94, the low-frequency component extraction unit 95, the low-frequency component calculation unit 96, and the threshold correction unit 97 included in the nanoparticle measurement device 9 may be implemented with either hardware such as a circuit or software (a computer program) executed by a central processing unit (CPU), or may be implemented with a combination of hardware and software.

In step S22, the timing signal generation unit 92 reads out a measurement parameter SPi−1 in the track TRi−1 from the storage unit 10. In step S 23, the reference position detection sensor 6 detects the slit 202 to generate a reference-position detection signal PDS. The reference position detection sensor 6 outputs the reference-position detection signal PDS to the reference-position detection unit 91 of the nanoparticle measurement device 9. The reference-position detection unit 91 outputs the reference-position detection signal PDS to the timing signal generation unit 92.

In step S24, the optical pickup 20 receives the reflected light from the specimen analysis disc 200, generates a light reception signal LRS, and outputs the signal to the light reception signal detection unit 93 of the nanoparticle measurement device 9. The light reception signal detection unit 93 outputs the light reception signal LRS to the low-frequency component extraction unit 95 and the measurement unit 94.

Figure 12:
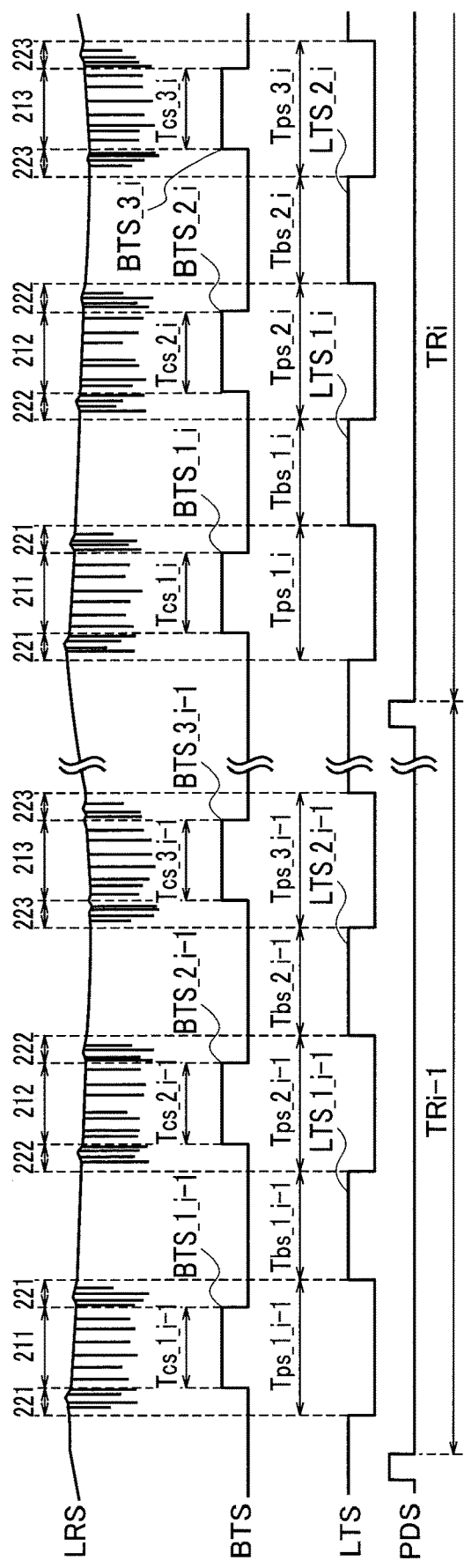
FIG. 12 is a timing chart illustrating a relationship between light reception signals, nanoparticle measurement timing signals, low-frequency component measurement timing signals, and reference position detection signals.

FIG. 12 is a timing chart illustrating a relationship between the light reception signals LRS, the nanoparticle measurement timing signals BTS, the low-frequency component measurement timing signals LTS, and the reference-position detection signals PDS. FIG. 12 only shows the light reception signals LRS, the nanoparticle measurement timing signals BTS, and the low-frequency component measurement timing signals LTS for measuring the nanoparticles 131 captured in the reaction regions 211 to 213 so as to correspond to FIG. 10.

Figure 13:
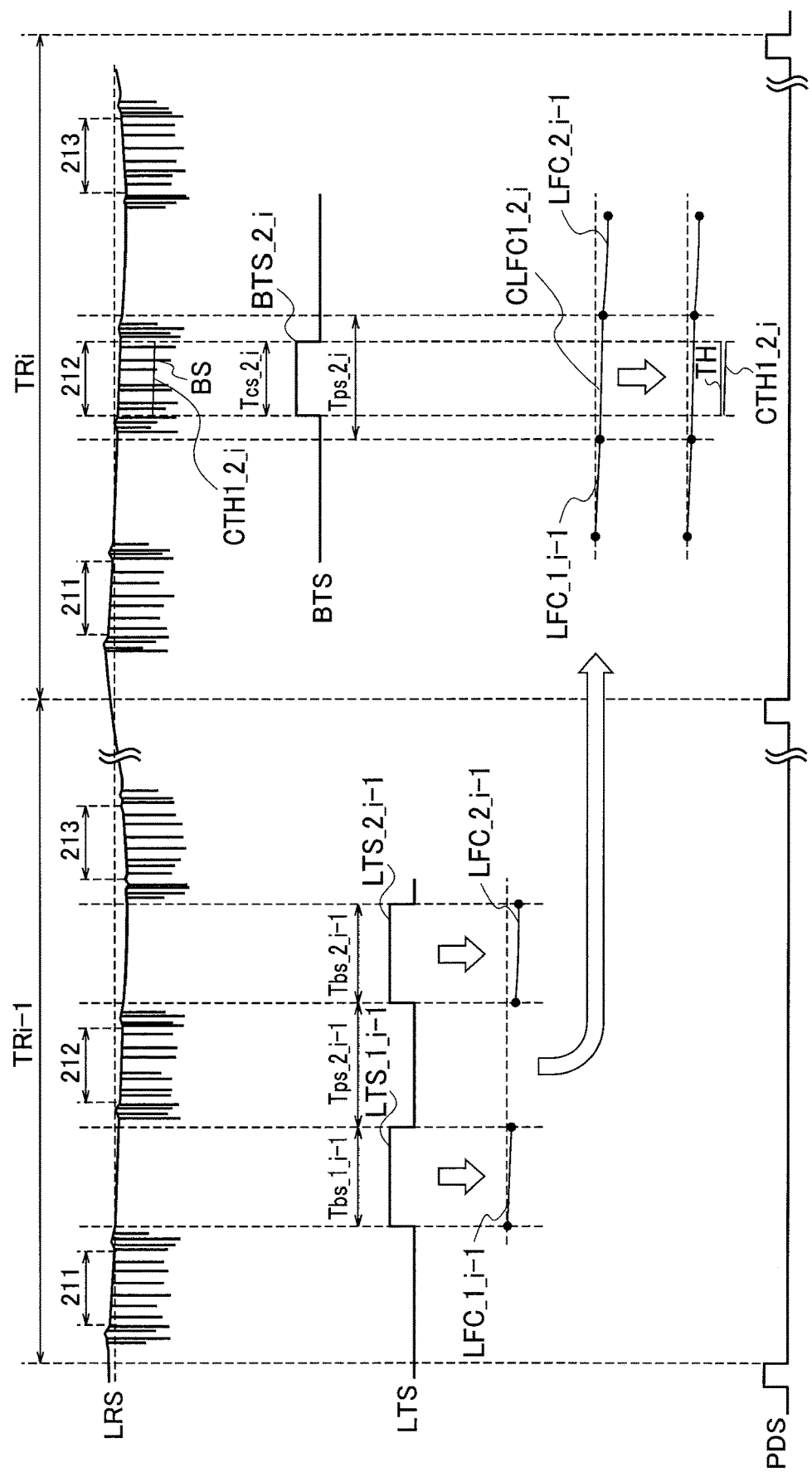
FIG. 13 is a timing chart illustrating a relationship between the light reception signals, the nanoparticle measurement timing signals, the low-frequency component measurement timing signals, low-frequency components, a threshold, and the reference position detection signals.

FIG. 13 is a timing chart illustrating a relationship between the light reception signals LRS, the low-frequency component measurement timing signals LTS, a threshold TH, a corrected threshold CTH1, and the reference-position detection signals PDS. FIG. 13 corresponds to FIG. 12.

When the reaction regions 210 (211 to 218) are formed by use of the detection-target-substance capture unit 100, the regions on the outside of the reaction regions 210 in the specimen analysis disc 200 are in contact with the seal members 304. The regions located at the outer circumferences of the reaction regions 210 and having a predetermined width contain noise components, and are thus defined as impurity regions 220 not to be measured. Reference numerals 221, 222, and 223 shown in FIG. 10 denote the respective impurity regions 220 distinguished from the corresponding reaction regions 211, 212, and 213.

The timing signal generation unit 92 generates the low-frequency component measurement timing signals LTS based on the measurement parameter SP and the reference-position detection signal PDS, and outputs the signals to the low-frequency component extraction unit 95. In the track TRi−1, the timing signal generation unit 92 generates the low-frequency component measurement timing signals LTS_1_$i$−1 and LTS_2_$i$−1 based on the measurement parameter SPi−1 and the reference-position detection signal PDS, as shown in FIG. 12 or FIG. 13.

The nanoparticle measurement device 9, the analysis device 1, and the analysis method according to a first embodiment are illustrated with a case in which the low-frequency component measurement timing signal LTS_1_$i$−1 is defined as a third timing signal, and the low-frequency component measurement timing signal LTS_2_$i$−1 is defined as a fourth timing signal. The timing signal generation unit 92 outputs the low-frequency component measurement timing signals LTS_1_$i$−1 and LTS_2_$i$−1 to the low-frequency component extraction unit 95.

In particular, in step S25, the timing signal generation unit 92 generates the low-frequency component measurement timing signal LTS_1_$i$−1 based on the measurement parameter SPi−1 and the reference-position detection signal PDS in the track TRi−1. The timing signal generation unit 92 outputs the low-frequency component measurement timing signal LTS_1_*i*–1 to the low-frequency component extraction unit 95.

The low-frequency component measurement timing signal LTS_1_*i*–1 is a gate pulse signal reaching a high level in a track interval Tbs_1_*i*–1 after the laser light 20*a* passes through a track interval Tps_1_*i*–1 corresponding to the impurity region 221 and the reaction region 211, for example.

The track interval Tbs_1_*i*–1 is an interval after the laser light 20*a* passes through the track interval Tps_1_*i*–1 and before the laser light 20*a* reaches a track interval Tps_2_*i*–1 corresponding to the impurity region 222 and the reaction region 212. Namely, the track interval Tbs_1_*i*–1 corresponds to an interval in which a gap between the impurity region 221 and the reaction region 211 and the impurity region 222 and the reaction region 212 is scanned with the laser light 20*a* in the track TRi–1.

The track interval Tbs, in which the region other than the reaction regions 210 and the impurity regions 220 is scanned with the laser light 20*a*, is defined as a second track interval, and a track interval Tcs, in which the reaction region 210 is scanned with the laser light 20*a*, is defined as a first track interval.

In step S26, the timing signal generation unit 92 generates the low-frequency component measurement timing signal LTS_2_*i*–1 based on the measurement parameter SPi–1 and the reference-position detection signal PDS in the track TRi–1. The timing signal generation unit 92 outputs the low-frequency component measurement timing signal LTS_2_*i*–1 to the low-frequency component extraction unit 95.

The low-frequency component measurement timing signal LTS_2_*i*–1 is a gate pulse signal reaching a high level in a track interval Tbs_2_*i*–1 after the laser light 20*a* passes through the track interval Tps_2_*i*–1 corresponding to the impurity region 222 and the reaction region 212, for example.

The track interval Tbs_2_*i*–1 is an interval after the laser light 20*a* passes through the track interval Tps_2_*i*–1 and before the laser light 20*a* reaches a track interval Tps_3_*i*–1 corresponding to the impurity region 223 and the reaction region 213. Namely, the track interval Tbs_2_*i*–1 corresponds to an interval in which a gap between the impurity region 222 and the reaction region 212 and the impurity region 223 and the reaction region 213 is scanned with the laser light 20*a* in the track TRi–1.

The low-frequency component extraction unit 95 extracts a low-frequency component LFC fluctuating because of a warp of the specimen analysis disc 200, from the light reception signal LRS according to the low-frequency component measurement timing signal LTS, and outputs the extracted component to the low-frequency component calculation unit 96. In particular, in step S27, the low-frequency component extraction unit 95 extracts a low-frequency component LFC_1_*i*–1 fluctuating because of a warp of the specimen analysis disc 200, from the light reception signal LRS according to the low-frequency component measurement timing signal LTS_1_*i*–1 in the track TRi–1, as shown in FIG. 13. The low-frequency component extraction unit 95 outputs the low-frequency component LFC_1_*i*–1 to the low-frequency component calculation unit 96. The nanoparticle measurement device 9, the analysis device 1, and the analysis method according to a first embodiment are illustrated with a case in which the low-frequency component LFC_1_*i*–1 is defined as a first low-frequency component.

In step S28, the low-frequency component extraction unit 95 extracts a low-frequency component LFC_2_*i*–1 fluctuating because of a warp of the specimen analysis disc 200, from the light reception signal LRS according to the low-frequency component measurement timing signal LTS_2_*i*–1 in the track TRi–1, as shown in FIG. 13. The low-frequency component extraction unit 95 outputs the low-frequency component LFC_2_*i*–1 to the low-frequency component calculation unit 96. The nanoparticle measurement device 9, the analysis device 1, and the analysis method according to a first embodiment are illustrated below with a case in which the low-frequency component LFC_2_*i*–1 is defined as a second low-frequency component.

In step S29, the low-frequency component calculation unit 96 computes the low-frequency component LFC_1_*i*–1 and the low-frequency component LFC_2_*i*–1 using a polynomial interpolation, for example, so as to calculate an interpolated low-frequency component CLFC1_2_*i* in a track interval Tps_2_*i* in the track TRi, as shown in FIG. 13. The interpolated low-frequency component CLFC1_2_*i* is a low-frequency component in the track interval Tps_2_*i* interpolated with the low-frequency component LFC_1_*i*–1 and the low-frequency component LFC_2_*i*–1. The low-frequency component calculation unit 96 outputs the interpolated low-frequency component CLFC1_2_*i* to the threshold correction unit 97.

In step S30, the threshold correction unit 97 corrects a predetermined threshold TH in accordance with the interpolated low-frequency component CLFC1_2_*i* to set a corrected threshold CTH1_2_*i* in the reaction region 212 in the track TRi, as shown in FIG. 13. The threshold correction unit 97 outputs the corrected threshold CTH1_2_*i* to the measurement unit 94.

In step S31 in the flow chart shown in FIG. 8C, the nanoparticle measurement device 9 controls the optical pickup drive circuit 8 to move the optical pickup 20 above the track TRi so that the laser light 20*a* is radiated to the track TRi of the specimen analysis disc 200. The track TRi is thus scanned with the laser light 20*a*.

In step S32, the timing signal generation unit 92 reads out a measurement parameter SPi in the track TRi from the storage unit 10. In step S 33, the reference position detection sensor detects the slit 202 to generate a reference-position detection signal PDS. The reference position detection sensor 6 outputs the reference-position detection signal PDS to the reference-position detection unit 91 of the nanoparticle measurement device 9. The reference-position detection unit 91 outputs the reference-position detection signal PDS to the timing signal generation unit 92.

In step S34, the optical pickup 20 receives the reflected light from the specimen analysis disc 200, generates a light reception signal LRS, and outputs the signal to the light reception signal detection unit 93 of the nanoparticle measurement device 9. The light reception signal detection unit 93 outputs the light reception signal LRS to the measurement unit 94 and the low-frequency component extraction unit 95.

The timing signal generation unit 92 generates nanoparticle measurement timing signals BTS_1_*i*, BTS_2_*i*, and BTS_3_*i* based on the measurement parameter SPi and the reference-position detection signal PDS in the track TRi, as shown in FIG. 12. The timing signal generation unit 92 outputs the nanoparticle measurement timing signals BTS_1_*i*, BTS_2_*i*, and BTS_3_*i* to the measurement unit 94.

For example, in step S35, the timing signal generation unit 92 generates the nanoparticle measurement timing signal BTS_2_$i$ based on the measurement parameter SPi and the reference-position detection signal PDS in the track TRi. The nanoparticle measurement timing signal BTS_2_$i$ is a gate pulse signal reaching a high level in a track interval Tcs_2_$i$ in which the reaction region 212 is scanned with the laser light 20a, for example, as shown in FIG. 10, FIG. 12, or FIG. 13. The timing signal generation unit 92 outputs the nanoparticle measurement timing signal BTS_2_$i$ to the measurement unit 94.

In step S36, the measurement unit 94 extracts pulse signals from the light reception signal LRS according to the nanoparticle measurement timing signal BTS_2_$i$. The measurement unit 94 compares the extracted pulse signals with the corrected threshold CTH1_2_$i$, and determines and extracts the pulse signals having a lower signal level than the corrected threshold CTH1_2_$i$ as the nanoparticle pulse signals BS, for example.

In step S37, the measurement unit 94 counts the nanoparticle pulse signals BS, so as to count the nanoparticles 131 in the track TRi in the reaction region 212. The measurement unit 94 stores the number of the nanoparticles 131 in association with the reaction region 212 and the track TRi in the storage unit 10.

When the nanoparticle measurement device 9 measures the nanoparticles 131 in the track TRi in the reaction region 212, the nanoparticle measurement device 9 extracts the low-frequency components LFC_1_$i$-1 and LFC_2_$i$-1 from the light reception signals LRS in the track intervals Tbs_1_$i$-1 and Tbs_2_$i$-1 before and after the laser light 20a passes through the reaction region 212 and the impurity region 222 in the track TRi-1 in front of the track TRi. The nanoparticle measurement device 9 calculates the interpolated low-frequency component CLFC1_2_$i$ in the track interval Tps_2_$i$ in the track TRi, in accordance with the low-frequency components LFC_1_$i$-1 and LFC_2_$i$-1.

The nanoparticle measurement device 9 corrects the predetermined threshold TH in accordance with the interpolated low-frequency component CLFC1_2_$i$ to set the corrected threshold CTH1_2_$i$ in the track TRi in the reaction region 212. The nanoparticle measurement device 9 extracts the nanoparticle pulse signals BS from the reception light signal LRS according to the nanoparticle measurement timing signal BTS_2_$i$ and the corrected threshold CTH1_2_$i$ so as to count the nanoparticle pulse signals BS.

In step S38, the nanoparticle measurement device 9 repeats the same processing from step S21 to step S37 for all of the tracks TR from the track TRs to the track TRe in all of the reaction regions 210 (211 to 218). The nanoparticle measurement device 9 thus counts the nanoparticles 131 in all of the tracks TR in all of the reaction regions 210.

The nanoparticle measurement device 9 counts the nanoparticles 131 in the respective reaction regions 211 to 218, so as to indirectly count the detection target substances 121 specifically bound to the nanoparticles 131 by the antigen-antibody reaction. The measurement unit 94 stores the number of the nanoparticles 131 in association with the reaction regions 210 and the tracks TR in the storage unit 10.

In step S39, the measurement unit 94 reads out the number of the nanoparticles 131 from the storage unit 10, and sums up the number of the nanoparticles 131 for each reaction region 210 (211 to 218). The measurement unit 94 directs the display unit 11 to display the measurement results per reaction region 210. For example, the measurement unit 94 displays the total number of the nanoparticles 131 per reaction region 210, or displays a distribution of the number of the nanoparticles 131 on the display unit 11.

When the nanoparticle measurement device 9, the analysis device 1, and the analysis method according to a first embodiment measure the nanoparticles 131 in the track TRi in the reaction region 212, the low-frequency components LFC_1_$i$-1 and LFC_2_$i$-1 are extracted from the reception light signals LRS in the track intervals Tbs_1_$i$-1 and Tbs_2_$i$-1 in front of and behind the reaction region 212 in the tangential direction in the track TRi-1 adjacent to the track TRi in the radial direction of the specimen analysis disc 200.

The nanoparticle measurement device 9, the analysis device 1, and the analysis method according to a first embodiment calculate the interpolated low-frequency component CLFC1_2_$i$ in the track interval Tps_2_$i$ in the track TRi in accordance with the low-frequency components LFC_1_$i$-1 and LFC_2_$i$-1. The nanoparticle measurement device 9, the analysis device 1, and the analysis method according to a first embodiment correct the predetermined threshold TH in accordance with the interpolated low-frequency component CLFC1_2_$i$ to set the corrected threshold CTH1_2_$i$ in the track TRi in the reaction region 212. The nanoparticle measurement device 9, the analysis device 1, and the analysis method according to a first embodiment extract the nanoparticle pulse signals BS from the reception light signal LRS according to the nanoparticle measurement timing signal BTS_2_$i$ and the corrected threshold CTH1_2_$i$ so as to count the nanoparticle pulse signals BS.

The nanoparticle measurement device 9, the analysis device 1, and the analysis method according to a first embodiment can reduce the influence of fluctuation of the low-frequency components derived from a warp of the specimen analysis disc 200 in the radial direction and in the tangential direction, so as to suppress a decrease in accuracy of detecting the nanoparticles 131 caused by the fluctuation of the low-frequency components.

Second Embodiment

A nanoparticle measurement device, an analysis device, and an analysis method according to a second embodiment are described below with reference to FIG. 7, FIG. 11, FIG. 14A, FIG. 14B, FIG. 14C, FIG. 14D, and FIG. 15. As shown in FIG. 7, the analysis device 401 according to a second embodiment has the same structure and executes the same processing as the analysis device 1 according to a first embodiment, but differs in the processing by the nanoparticle measurement device 409 from the nanoparticle measurement device 9. The processing by the nanoparticle measurement device 409 is described below. The same elements and signals as in the analysis device 1 according to a first embodiment are denoted by the same reference numerals for brevity.

As shown in FIG. 7, the analysis device 401 includes the turntable 2, the clamper 3, the turntable drive unit 4, the turntable drive circuit 5, and the reference-position detection sensor 6. The analysis device 401 further includes the guide shaft 7, the optical pickup 20, the optical pickup drive circuit 8, the nanoparticle measurement device 409, the storage unit 10, and the display unit 11. The nanoparticle measurement device 409 serves as a controller to control the turntable drive circuit 5 and the optical pickup drive circuit 8. The analysis device 401 does not necessarily include the display unit 11, and an external display unit may be used instead.

The nanoparticle measurement device 409 counts the number of the nanoparticles 131 labeling the detection target substances 121 from the extracted nanoparticle pulse signals BS. The nanoparticle measurement device 409 directs the storage unit 10 to store the number of the nanoparticles 131 per nanoparticle measurement timing signal BTS in each reaction region 210. The nanoparticle measurement device 409 adds up the number of the nanoparticles 131 in each reaction region 210 and displays the sum on the display unit 11. The number of the nanoparticles 131 displayed corresponds to the number of the detection target substances 121 specifically bound to the nanoparticles 131.

The analysis method of analyzing the detection target substances 121 by the analysis device 401, more particularly the method of analyzing the nanoparticles 131 labeling the detection target substances 121, is described below with reference to FIG. 11, FIG. 14A, FIG. 14B, FIG. 14C, FIG. 14D, and FIG. 15. FIG. 14A, FIG. 14B, FIG. 14C, and FIG. 14D are flow charts illustrating the analysis method of analyzing the detection target substances 121 by the analysis device 401.

Figure 14A:
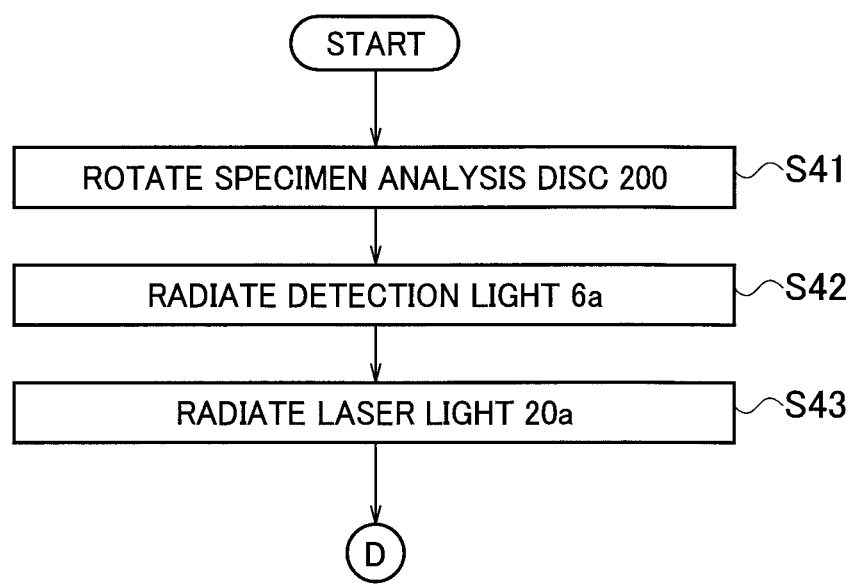
FIG. 14A is a flow chart for illustrating an analysis method by the analysis device according to a second embodiment.

In step S41 in the flow chart shown in FIG. 14A, the nanoparticle measurement device 409 controls the turntable drive circuit 5 to direct the turntable drive unit 4 to turn the turntable 2 so that the specimen analysis disc 200 rotates at a constant linear velocity.

In step S42, the nanoparticle measurement device 409 directs the reference-position detection sensor 6 to emit the detection light 6a to the specimen analysis disc 200. In step S43, the nanoparticle measurement device 409 directs the optical pickup 20 to emit the laser light 20a to the specimen analysis disc 200. Step S43 is not necessarily performed after step S42. Step S42 may be performed after step S43, or step S42 and step S43 may be performed simultaneously.

A case of measuring the nanoparticles 131 in the track TRi in the reaction region 212 is described below. For illustration purposes, only signal processing of measuring the nanoparticles 131 in the track TRi in the reaction region 212 is described below.

Figure 14B:
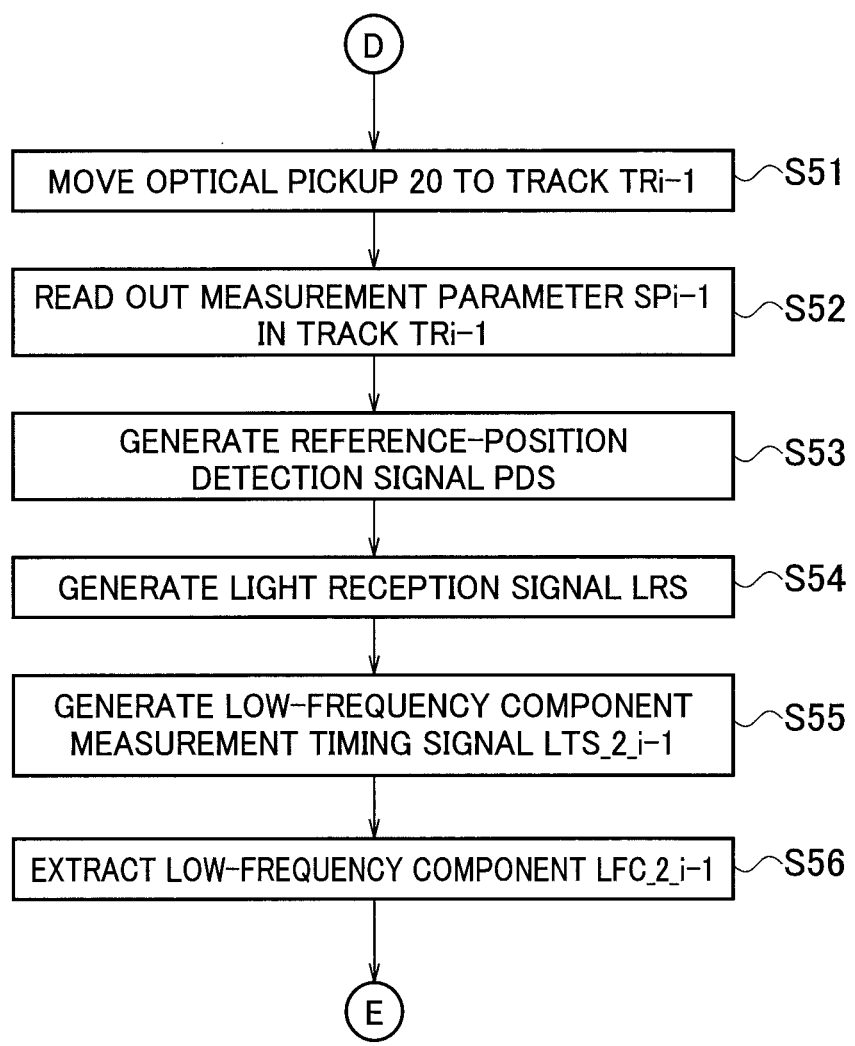
FIG. 14B is a flow chart for illustrating the analysis method by the analysis device according to a second embodiment.

In step S51 in the flow chart shown in FIG. 14B, the nanoparticle measurement device 409 controls the optical pickup drive circuit 8 to move the optical pickup 20 above the track TRi−1 so that the laser light 20a is radiated to the track TRi−1 of the specimen analysis disc 200. The track TRi−1 is thus scanned with the laser light 20a. The nanoparticle measurement device 409, the analysis device 401, and the analysis method according to a second embodiment are illustrated with a case in which the track TRi is a third track, and the track TRi−1 is a fourth track.

As shown in FIG. 11, the nanoparticle measurement device 409 includes the reference-position detection unit 91, the timing signal generation unit 92, the light reception signal detection unit 93, a measurement unit 494, a low-frequency component extraction unit 495, a low-frequency component calculation unit 496, and a threshold correction unit 497.

The nanoparticle measurement device 409, and the reference-position detection unit 91, the timing signal generation unit 92, the light reception signal detection unit 93, the measurement unit 494, the low-frequency component extraction unit 495, the low-frequency component calculation unit 496, and the threshold correction unit 497 included in the nanoparticle measurement device 409 may be implemented with either hardware such as a circuit or software (a computer program) executed by a CPU, or may be implemented with a combination of hardware and software.

In step S52, the timing signal generation unit 92 reads out a measurement parameter SPi−1 in the track TRi−1 from the storage unit 10. In step S53, the reference position detection sensor 6 detects the slit 202 to generate a reference-position detection signal PDS. The reference position detection sensor 6 outputs the reference-position detection signal PDS to the reference-position detection unit 91 of the nanoparticle measurement device 409. The reference-position detection unit 91 outputs the reference-position detection signal PDS to the timing signal generation unit 92.

In step S54, the optical pickup 20 receives the reflected light from the specimen analysis disc 200, generates a light reception signal LRS, and outputs the signal to the light reception signal detection unit 93 of the nanoparticle measurement device 409. The light reception signal detection unit 93 outputs the light reception signal LRS to the low-frequency component extraction unit 495 and the measurement unit 494.

Figure 15:
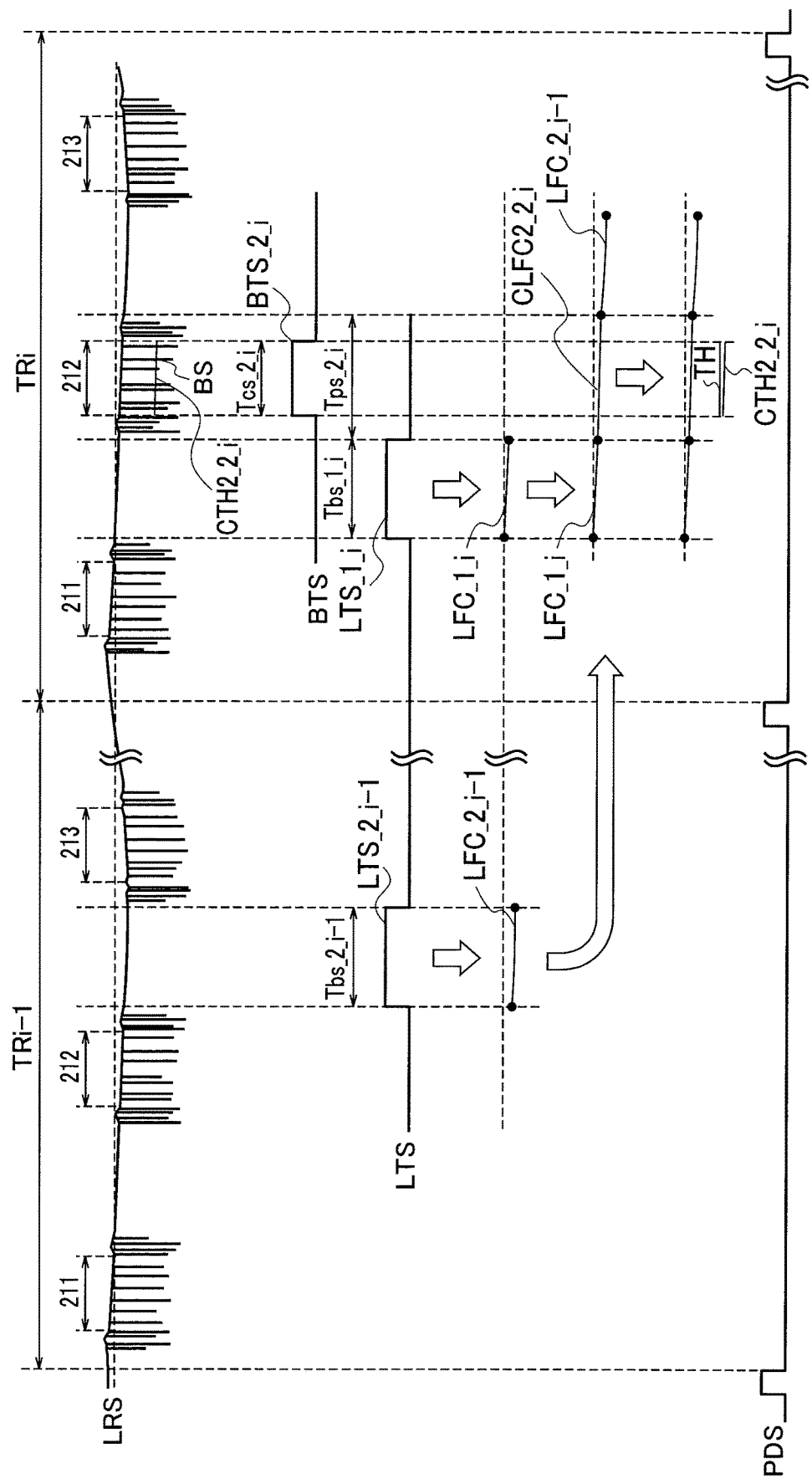
FIG. 15 is a timing chart illustrating a relationship between light reception signals, nanoparticle measurement timing signals, low-frequency component measurement timing signals, low-frequency components, a threshold, and reference position detection signals.

FIG. 15 is a timing chart illustrating a relationship between the light reception signals LRS, the low-frequency component measurement timing signals LTS, low-frequency components, the threshold TH, a corrected threshold CTH2, and the reference-position detection signals PDS. FIG. 15 corresponds to FIG. 12 or FIG. 13.

The timing signal generation unit 92 generates the low-frequency component measurement timing signals LTS based on the measurement parameter SP and the reference-position detection signal PDS, and outputs the signals to the low-frequency component extraction unit 495. In the track TRi−1, the timing signal generation unit 92 generates the low-frequency component measurement timing signal LTS_2_i−1 based on the measurement parameter SPi−1 and the reference-position detection signal PDS, as shown in FIG. 12 or FIG. 15.

In particular, in step S55, the timing signal generation unit 92 generates the low-frequency component measurement timing signal LTS_2_i−1 based on the measurement parameter SPi−1 and the reference-position detection signal PDS in the track TRi−1. The timing signal generation unit 92 outputs the low-frequency component measurement timing signal LTS_2_i−1 to the low-frequency component extraction unit 495.

The low-frequency component measurement timing signal LTS_2_i−1 is a gate pulse signal reaching a high level in the track interval Tbs_2_i−1 after the laser light 20a passes through the track interval Tps_2_i−1 corresponding to the impurity region 222 and the reaction region 212, for example.

The track interval Tbs_2_i−1 is an interval after the laser light 20a passes through the track interval Tps_2_i−1 and before the laser light 20a reaches the track interval Tps_3_i−1 corresponding to the impurity region 223 and the reaction region 213. Namely, the track interval Tbs_2_i−1 corresponds to an interval in which a gap between the impurity region 222 and the reaction region 212 and the impurity region 223 and the reaction region 213 is scanned with the laser light 20a in the track TRi−1.

The low-frequency component extraction unit 495 extracts a low-frequency component LFC fluctuating because of a warp of the reaction region 210 of the specimen analysis disc 200, from the light reception signal LRS according to the low-frequency component measurement timing signal LTS, and outputs the extracted component to the low-frequency component calculation unit 496. In particular, in step S56, the low-frequency component extraction unit 495 extracts a low-frequency component LFC_2_i−1 fluctuating because of a warp of the specimen analysis disc 200, from the light reception signal LRS according to the low-frequency component measurement timing signal LTS_2_i−1 in the track TRi−1, as shown in FIG. 15. The low-frequency component extraction unit 495 outputs the low-frequency component LFC_2_i−1 to the low-frequency component calculation unit 496. The nanoparticle measurement device 409, the analysis device 401, and the analysis method according to a second embodiment are illustrated with a case in which the low-frequency component LFC_2_i−1 is defined as a third low-frequency component.

Figure 14C:
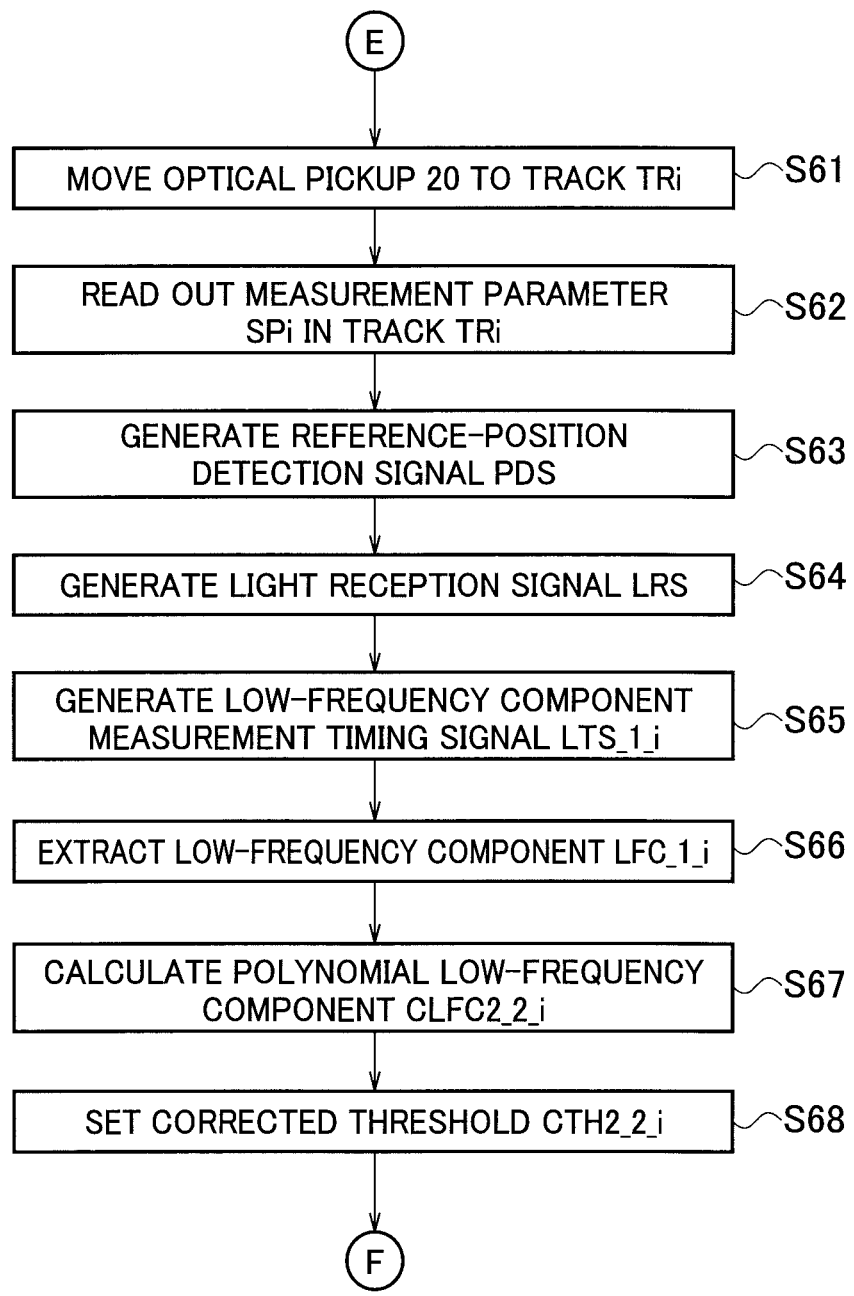
FIG. 14C is a flow chart for illustrating the analysis method by the analysis device according to a second embodiment.

In step S61 in the flow chart shown in FIG. 14C, the nanoparticle measurement device 409 controls the optical pickup drive circuit 8 to move the optical pickup 20 above the track TRi so that the laser light 20a is radiated to the track TRi of the specimen analysis disc 200. The track TRi is thus scanned with the laser light 20a.

In step S62, the timing signal generation unit 92 reads out a measurement parameter SPi in the track TRi from the storage unit 10. In step S 63, the reference position detection sensor detects the slit 202 to generate a reference-position detection signal PDS. The reference position detection sensor 6 outputs the reference-position detection signal PDS to the reference-position detection unit 91 of the nanoparticle measurement device 409. The reference-position detection unit 91 outputs the reference-position detection signal PDS to the timing signal generation unit 92.

In step S64, the optical pickup 20 receives the reflected light from the specimen analysis disc 200, generates a light reception signal LRS, and outputs the signal to the light reception signal detection unit 93 of the nanoparticle measurement device 409. The light reception signal detection unit 93 outputs the light reception signal LRS to the low-frequency component extraction unit 495 and the measurement unit 494.

In step S65, the timing signal generation unit 92 generates the low-frequency component measurement timing signal LTS_1_i based on the measurement parameter SPi and the reference-position detection signal PDS in the track TRi, as shown in FIG. 12 or FIG. 15. The timing signal generation unit 92 outputs the low-frequency component measurement timing signal LTS_1_i to the low-frequency component extraction unit 495. The nanoparticle measurement device 409, the analysis device 401, and the analysis method according to a second embodiment are illustrated with a case in which the low-frequency component measurement timing signal LTS_2_i−1 is defined as a fifth timing signal, and the low-frequency component measurement timing signal LTS_1_i is defined as a sixth timing signal.

The low-frequency component measurement timing signal LTS_1_i is a gate pulse signal reaching a high level in the track interval Tbs_1_i before the laser light 20a reaches the track interval Tps_2_i corresponding to the impurity region 222 and the reaction region 212, for example.

The track interval Tbs_1_i is an interval after the laser light 20a passes through the track interval Tps_1_i and before the laser light 20a reaches the track interval Tps_2_i corresponding to the impurity region 222 and the reaction region 212. Namely, the track interval Tbs_1_i corresponds to an interval in which a gap between the impurity region 221 and the reaction region 211 and the impurity region 222 and the reaction region 212 is scanned with the laser light 20a in the track TRi.

In step S66, the low-frequency component extraction unit 495 extracts a low-frequency component LFC_1_i fluctuating because of a warp of the reaction region 210 of the specimen analysis disc 200, from the light reception signal LRS according to the low-frequency component measure-ment timing signal LTS_1_i in the track TRi, as shown in FIG. 15. The low-frequency component extraction unit 495 outputs the low-frequency component LFC_1_i to the low-frequency component calculation unit 496. The nanoparticle measurement device 409, the analysis device 401, and the analysis method according to a second embodiment are illustrated with a case in which the low-frequency component LFC_1_i is defined as a fourth low-frequency component.

In step S67, the low-frequency component calculation unit 496 computes the low-frequency component LFC_2_i−1 and the low-frequency component LFC_1_i using a polynomial interpolation, for example, so as to calculate an interpolated low-frequency component CLFC2_2_i in the track interval Tps_2_i in the track TRi, as shown in FIG. 15. The interpolated low-frequency component CLFC2_2_i is a low-frequency component in the track interval Tps_2_i interpolated with the low-frequency component LFC_2_i−1 and the low-frequency component LFC_1_i. The low-frequency component calculation unit 496 outputs the interpolated low-frequency component CLFC2_2_i to the threshold correction unit 497.

In step S68, the threshold correction unit 497 corrects the predetermined threshold TH in accordance with the interpolated low-frequency component CLFC2_2_i to set a corrected threshold CTH2_2_i in the track TRi in the reaction region 212, as shown in FIG. 15. The threshold correction unit 497 outputs the corrected threshold CTH2_2_i to the measurement unit 494.

The timing signal generation unit 92 generates the nanoparticle measurement timing signals BTS_1_i, BTS_2_i, and BTS_3_i based on the measurement parameter SPi and the reference-position detection signal PDS in the track TRi, as shown in FIG. 12. The timing signal generation unit 92 outputs the nanoparticle measurement timing signals BTS_1_i, BTS_2_i, and BTS_3_i to the measurement unit 494.

Figure 14D:
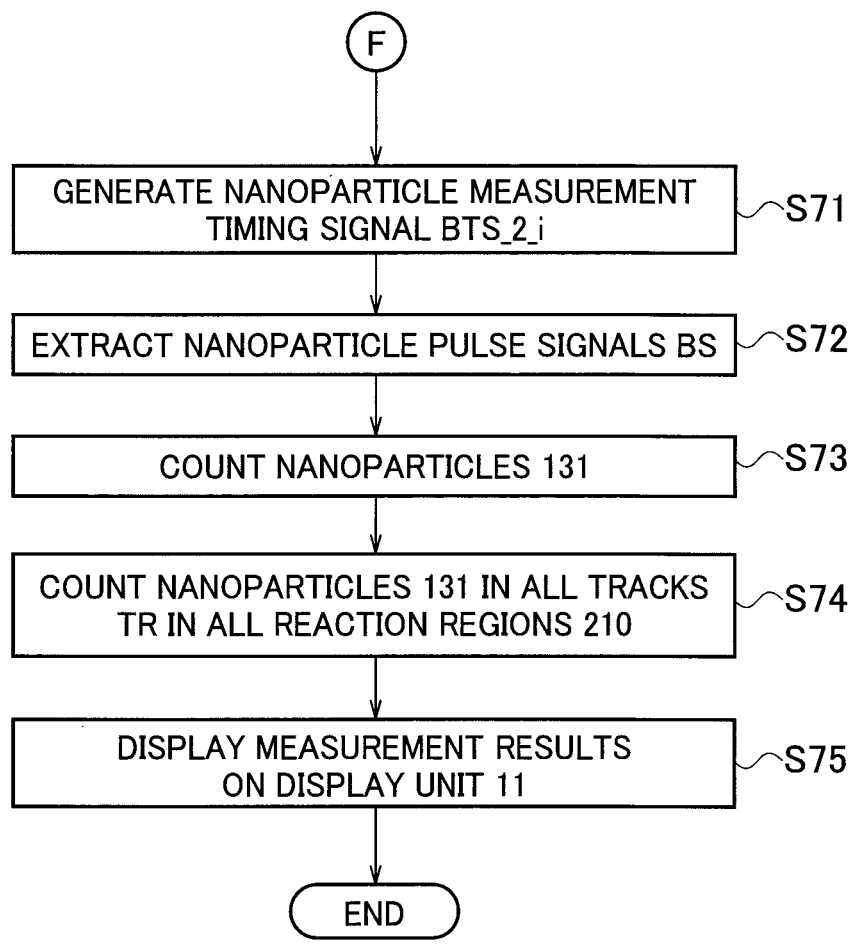
FIG. 14D is a flow chart for illustrating the analysis method by the analysis device according to a second embodiment.

For example, in step S71 in the flow chart shown in FIG. 14D, the timing signal generation unit 92 generates the nanoparticle measurement timing signal BTS_2_i based on the measurement parameter SPi and the reference-position detection signal PDS in the track TRi. The nanoparticle measurement timing signal BTS_2_i is a gate pulse signal reaching a high level in the track interval Tcs_2_i in which the reaction region 212 is scanned with the laser light 20a, for example, as shown in FIG. 10, FIG. 12, or FIG. 15. The timing signal generation unit 92 outputs the nanoparticle measurement timing signal BTS_2_i to the measurement unit 494.

In step S72, the measurement unit 494 extracts pulse signals from the light reception signal LRS according to the nanoparticle measurement timing signal BTS_2_i. The measurement unit 494 compares the extracted pulse signals with the corrected threshold CTH2_2_i, and determines and extracts the pulse signals having a lower signal level than the corrected threshold CTH2_2_i as the nanoparticle pulse signals BS, for example.

In step S73, the measurement unit 494 counts the nanoparticle pulse signals BS, so as to count the nanoparticles 131 in the track TRi in the reaction region 212. The measurement unit 494 stores the number of the nanoparticles 131 in association with the reaction region 212 and the track TRi in the storage unit 10.

When the nanoparticle measurement device 409 measures the nanoparticles 131 in the track TRi in the reaction region 212, the nanoparticle measurement device 409 extracts the low-frequency component LFC_2_i−1 from the light reception signal LRS in the track interval Tbs_2_$i$–1 after the laser light 20a passes through the reaction region 212 and the impurity region 222 in the track TRi–1 in front of the track TRi.

The nanoparticle measurement device 409 extracts the low-frequency component LFC_1_$i$ from the light reception signal LRS in the track interval Tbs_1_$i$ before the laser light 20a reaches the reaction region 212 and the impurity region 222 in the track TRi. The nanoparticle measurement device 409 calculates the interpolated low-frequency component CLFC22$i$ in the track interval Tps_2_$i$ in the track TRi in accordance with the low-frequency components LFC_2_$i$–1 and LFC_1_$i$.

The nanoparticle measurement device 409 corrects the predetermined threshold TH in accordance with the interpolated low-frequency component CLFC2_2_$i$ to set the corrected threshold CTH2_2_$i$ in the track TRi in the reaction region 212. The nanoparticle measurement device 409 extracts the nanoparticle pulse signals BS from the reception light signal LRS according to the nanoparticle measurement timing signal BTS_2_$i$ and the corrected threshold CTH2_2_$i$ so as to count the nanoparticle pulse signals BS.

In step S74, the nanoparticle measurement device 409 repeats the same processing from step S51 to step S73 for all of the tracks TR from the track TRs to the track TRe in all of the reaction regions 210 (211 to 218). The nanoparticle measurement device 409 thus counts the nanoparticles 131 in all of the tracks TR in all of the reaction regions 210.

The nanoparticle measurement device 409 counts the nanoparticles 131 in the respective reaction regions 211 to 218, so as to indirectly count the detection target substances 121 specifically bound to the nanoparticles 131 by the antigen-antibody reaction. The measurement unit 494 stores the number of the nanoparticles 131 in association with the reaction regions 210 and the tracks TR in the storage unit 10.

In step S75, the measurement unit 494 reads out the number of the nanoparticles 131 from the storage unit 10, and sums up the number of the nanoparticles 131 for each reaction region 210 (211 to 218). The measurement unit 494 directs the display unit 11 to display the measurement results per reaction region 210. For example, the measurement unit 494 displays the total number of the nanoparticles 131 per reaction region 210, or displays a distribution of the number of the nanoparticles 131 on the display unit 11.

When the nanoparticle measurement device 409, the analysis device 401, and the analysis method according to a second embodiment measure the nanoparticles 131 in the track TRi in the reaction region 212, the low-frequency component LFC_2_$i$–1 is extracted from the reception light signal LRS in the track interval Tbs_2_$i$–1 behind the reaction region 212 in the tangential direction in the track TRi–1 adjacent to the track TRi in the radial direction of the specimen analysis disc 200.

The nanoparticle measurement device 409, the analysis device 401, and the analysis method according to a second embodiment further extract the low-frequency component LFC_1_$i$ from the reception light signal LRS in the track interval Tbs_1_$i$ in front of the reaction region 212 in the tangential direction in the track TRi. The nanoparticle measurement device 409, the analysis device 401, and the analysis method according to a second embodiment calculate the interpolated low-frequency component CLFC2_2_$i$ in the track interval Tps_2_$i$ in the track TRi in accordance with the low-frequency components LFC_2_$i$–1 and LFC_1_$i$.

The nanoparticle measurement device 409, the analysis device 401, and the analysis method according to a second embodiment correct the predetermined threshold TH in accordance with the interpolated low-frequency component CLFC2_2_$i$ to set the corrected threshold CTH2_2_$i$ in the track TRi in the reaction region 212. The nanoparticle measurement device 409, the analysis device 401, and the analysis method according to a second embodiment extract the nanoparticle pulse signals BS from the reception light signal LRS according to the nanoparticle measurement timing signal BTS_2_$i$ and the corrected threshold CTH2_2_$i$ so as to count the nanoparticle pulse signals BS.

The nanoparticle measurement device 409, the analysis device 401, and the analysis method according to a second embodiment can reduce the influence of fluctuation of the low-frequency components derived from a warp of the specimen analysis disc 200 in the radial direction and in the tangential direction, so as to suppress a decrease in accuracy of detecting the nanoparticles 131 caused by fluctuation of the low-frequency components.

It should be understood that the present invention is not intended to be limited to first or second embodiment described above, and various modifications will be apparent to those skilled in the art without departing from the scope of the present invention.

The nanoparticle measurement device 9 in the analysis device 1 according to a first embodiment includes the reference-position detection unit 91, the timing signal generation unit 92, the light reception signal detection unit 93, the measurement unit 94, the low-frequency component extraction unit 95, the low-frequency component calculation unit 96, and the threshold correction unit 97, as shown in FIG. 11. Alternatively, for example, the nanoparticle measurement device 9 in the analysis device 1 according to a first embodiment may include the timing signal generation unit 92, the measurement unit 94, the low-frequency component extraction unit 95, the low-frequency component calculation unit 96, and the threshold correction unit 97.

In such a case, the analysis device 1 includes the turntable 2, the clamper 3, the turntable drive unit 4, the turntable drive circuit 5, the reference-position detection sensor 6, the guide shaft 7, the optical pickup 20, the optical pickup drive circuit 8, a controller, the storage unit 10, and the display unit 11, wherein the controller includes the reference-position detection unit 91, the light reception signal detection unit 93, and the nanoparticle measurement device 9.

The nanoparticle measurement device 409 in the analysis device 401 according to a second embodiment includes the reference-position detection unit 91, the timing signal generation unit 92, the light reception signal detection unit 93, the measurement unit 494, the low-frequency component extraction unit 495, the low-frequency component calculation unit 496, and the threshold correction unit 497, as shown in FIG. 11. Alternatively, for example, the nanoparticle measurement device 409 in the analysis device 401 according to a second embodiment may include the timing signal generation unit 92, the measurement unit 494, the low-frequency component extraction unit 495, the low-frequency component calculation unit 496, and the threshold correction unit 497.

In such a case, the analysis device 401 includes the turntable 2, the clamper 3, the turntable drive unit 4, the turntable drive circuit 5, the reference-position detection sensor 6, the guide shaft 7, the optical pickup 20, the optical pickup drive circuit 8, a controller, the storage unit 10, and the display unit 11, wherein the controller includes the reference-position detection unit 91, the light reception signal detection unit 93, and the nanoparticle measurement device 409.

FIG. 12, FIG. 13, or FIG. 15 indicates the nanoparticle measurement timing signals BTS and the low-frequency component measurement timing signals LTS as rectangular gate pulse signals which rise at the start point and fall at the endpoint. The nanoparticle measurement timing signals BTS and the low-frequency component measurement timing signals LTS are not limited to the gate pulse signals and may be trigger pulse signals which reach a high level at the start point and at the end point.

FIG. 13 or FIG. 15 indicates the two sampling points for the respective low-frequency components when the interpolated low-frequency component CLFC is calculated from the low-frequency components LFC extracted from the light reception signal LRS in accordance with the low-frequency component measurement timing signal LTS. The number of the sampling points for the respective low-frequency components LFC is not limited to two, and may be three or more.

When the nanoparticles 131 in the track TRi in the reaction region 212 are measured, the nanoparticle measurement device 9 or 409 may extract the low-frequency components LFC_1_$i$ and LFC_1_$i$ from the light reception signals LRS in the track intervals Tbs_1_$i$ and Tbs_2_$i$ in front of and behind the track interval Tps_2_$i$ corresponding to the impurity region 222 and the reaction region 212 in accordance with the low-frequency component measurement timing signals LTS_1_$i$ and LTS_2$i$ in the track TRi.

The nanoparticle measurement device 9 or 409 extracts the light reception signal LRS in the track interval Tcs_2_$i$ according to the nanoparticle measurement timing signal BTS_2_$i$. The nanoparticle measurement device 9 or 409 stores the extracted light reception signal LRS and the low-frequency components LFC_1_$i$ and LFC_1_$i$ in the storage unit 10. The nanoparticle measurement device 9 or 409 reads out the low-frequency components LFC_1_$i$ and LFC_1_$i$ from the storage unit 10, and calculates the interpolated low-frequency component CLFC_2_$i$ in the track interval Tps_2_$i$ in the track TRi in accordance with the low-frequency components LFC_1_$i$ and LFC_1_$i$.

The nanoparticle measurement device 9 or 409 corrects the predetermined threshold TH in accordance with the interpolated low-frequency component CLFC_2_$i$ to set a corrected threshold CTH_2_$i$ in the track TRi in the reaction region 212. The nanoparticle measurement device 9 or 409 reads out, from the storage unit 10, the light reception signal LRS extracted from the nanoparticle measurement timing signal BTS_2_$i$. The nanoparticle measurement device 9 or 409 extracts and counts the nanoparticle signals BS from the reception light signal LRS according to the corrected threshold CTH_2_$i$.

The nanoparticle measurement device, the analysis device, and the analysis method described above can achieve the effects similar to the nanoparticle measurement device 9 or 409, the analysis device 1 or 401, and the analysis method according to first or second embodiment.

What is claimed is:

1. A nanoparticle measurement device comprising:
 a timing signal generation unit configured to generate a first timing signal corresponding to a first track interval in a reaction region formed in a disc for specimen analysis having a plurality of tracks on which nanoparticles binding to substances to be detected are captured per track, and a second timing signal corresponding to a second track interval different from the first track interval in the reaction region, the tracks being formed from an inner side to an outer side of the disc for specimen analysis;
 a low-frequency component extraction unit configured to extract a low-frequency component which is a frequency fluctuating because of a warp of the disc for specimen analysis from a light reception signal according to the second timing signal, the light reception signal being generated when a laser light is radiated to the reaction region and a reflected light is received from the reaction region;
 a low-frequency component calculation unit configured to calculate an interpolated low-frequency component corresponding to the first track interval from the light reception signal and interpolated in accordance with the low-frequency component;
 a threshold correction unit configured to correct a predetermined threshold pulse signal in accordance with the interpolated low-frequency component to set a corrected threshold pulse signal; and
 a measurement unit configured to extract nanoparticle pulse signals from the light reception signal according to the first timing signal and the corrected threshold pulse signal, and count the nanoparticle pulse signals, so as to count the nanoparticles captured in the first track interval in the reaction region.

2. The nanoparticle measurement device according to claim 1, wherein the disc for specimen analysis comprises a region, defined as an impurity region, located at an outer circumference of the reaction region and having a predetermined width.

3. The nanoparticle measurement device according to claim 2, wherein, when the laser light is radiated to the reaction region, the reflected light is received from the reaction region to generate the light reception signal, and the nanoparticles captured in a first track of the plurality of tracks in the reaction region are counted in accordance with the light reception signal,
 the timing signal generation unit generates a third timing signal which is the second timing signal in a track interval before the laser light reaches the reaction region and the impurity region, and generates a fourth timing signal which is the second timing signal in a track interval after the laser light passes through the reaction region and the impurity region, in a second track different from the first track,
 the low-frequency component extraction unit extracts a first low-frequency component from the light reception signal according to the third timing signal, and extracts a second low-frequency component from the light reception signal according to the fourth timing signal, and
 the low-frequency component calculation unit calculates the interpolated low-frequency component corresponding to the first track interval in accordance with the first and second low-frequency components.

4. The nanoparticle measurement device according to claim 3, wherein, when the laser light is radiated to the reaction region, the reflected light is received from the reaction region to generate light reception signal, and the nanoparticles captured in a third track of the plurality of tracks in the reaction region are counted in accordance with the light reception signal,
 the timing signal generation unit generates a fifth timing signal which is the second timing signal in a track interval after the laser light passes through the reaction region and the impurity region in a fourth track different from the third track in a fourth track different from the third track, and generates a sixth timing signal which is the second timing signal in a track interval before the laser light reaches the reaction region and the impurity region in the third track, the low-frequency component extraction unit extracts a third low-frequency component from the light reception signal according to the fifth timing signal, and a fourth low-frequency component from the light reception signal according to the sixth timing signal, and the low-frequency component calculation unit calculates an interpolated low-frequency component corresponding to the first track interval in accordance with the third and fourth low-frequency components.

5. An analysis device comprising:
a turntable holding a disc for specimen analysis;
a turntable drive unit configured to rotate the turntable;
a turntable drive circuit configured to control the turntable drive unit;
an optical pickup driven in a direction perpendicular to a rotation axis of the turntable, and configured to emit a laser light to a reaction region, receive a reflected light from the reaction region, and generate a light reception signal;
an optical pickup drive circuit configured to control an operation of the optical pickup; and
a controller configured to control the turntable drive circuit and the optical pickup drive circuit, wherein
the controller comprises the nanoparticle measurement device according to claim 1.

6. An analysis method comprising:
rotating a disc for specimen analysis having a plurality of tracks formed from an inner side to an outer side and having a reaction region on which nanoparticles binding to substances to be detected are captured per track;
radiating a laser light to the reaction region per track;
receiving a reflected light from the reaction region to generate a light reception signal;
generating a first timing signal corresponding to a first track interval in the reaction region, and a second timing signal corresponding to a second track interval different from the first track interval in the reaction region;
extracting a low-frequency component which is a frequency fluctuating because of a warp of the disc for specimen analysis from the light reception signal according to the second timing signal;
calculating an interpolated low-frequency component corresponding to the first track interval and interpolated in accordance with the low-frequency component;
correcting a predetermined threshold pulse signal in accordance with the interpolated low-frequency component to set a corrected threshold pulse signal;
extracting nanoparticle pulse signals from the light reception signal according to the first timing signal and the corrected threshold pulse signal; and
counting the nanoparticle pulse signals so as to count the nanoparticles captured in the first track interval in the reaction region.

* * * * *